(12) United States Patent
Allred et al.

(10) Patent No.: US 6,756,417 B2
(45) Date of Patent: Jun. 29, 2004

(54) DENTAL BONDING COMPOSITIONS FOR ADHERING AMALGAM RESTORATIVES TO DENTAL SUBSTRATES

(75) Inventors: Peter M. Allred, Riverton, UT (US); Neil T. Jessop, Colton, CA (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 83 days.

(21) Appl. No.: 10/098,709

(22) Filed: Mar. 13, 2002

(65) Prior Publication Data

US 2003/0199600 A1 Oct. 23, 2003

(51) Int. Cl.$^7$ .............................. C08F 2/50; A61C 5/08; A61C 5/04
(52) U.S. Cl. .............................. 522/13; 522/24; 522/47; 522/74; 522/81; 522/83; 522/104; 522/107; 522/120; 522/113; 522/129; 522/130; 522/150; 522/153; 522/178; 522/182; 523/113; 523/115; 523/116; 523/118; 433/226; 433/217.1; 433/219; 433/228.1
(58) Field of Search .............................. 433/226, 217.1, 433/219, 228.1; 523/113, 115, 116, 118; 522/13, 24, 47, 74, 81, 83, 104, 107, 113, 120, 129, 130, 150, 153, 178, 182

(56) References Cited

U.S. PATENT DOCUMENTS

| | | |
|---|---|---|
| 4,064,629 A | 12/1977 | Stoner et al. |
| 4,155,890 A | 5/1979 | Hofaker-Freifrau |
| 4,225,476 A | 9/1980 | Hammer et al. |
| 4,247,575 A | 1/1981 | O'Connell et al. |
| 4,362,510 A | 12/1982 | Brauer et al. |
| 4,362,842 A | 12/1982 | Masuhara et al. |
| 4,486,179 A | 12/1984 | Brauer et al. |
| 4,514,342 A | 4/1985 | Billington et al. |
| 4,542,168 A | 9/1985 | Chang et al. |
| 4,657,941 A | 4/1987 | Blackwell et al. |
| 4,711,913 A | 12/1987 | Tateosian et al. |
| 4,719,149 A | 1/1988 | Aasen et al. |
| 4,738,722 A | 4/1988 | Ibsen et al. |
| 4,759,798 A | 7/1988 | von Nostiz |
| 4,806,381 A | 2/1989 | Engelbrecht et al. |
| 4,830,616 A | 5/1989 | Okuda et al. |
| RE33,100 E | 10/1989 | Ibsen et al. |
| 4,880,660 A | 11/1989 | Aasen et al. |
| 4,950,697 A | 8/1990 | Chang et al. |
| 4,966,934 A | 10/1990 | Huang et al. |
| 4,983,644 A | 1/1991 | Mukai et al. |
| 4,986,754 A | 1/1991 | Chang et al. |
| 5,147,903 A | 9/1992 | Podszun et al. |
| 5,154,762 A | 10/1992 | Mitra et al. |
| 5,158,825 A | 10/1992 | Altwirth |
| 5,178,870 A | 1/1993 | Schaeken et al. |
| 5,192,802 A | 3/1993 | Rencher |
| 5,252,121 A | 10/1993 | Arnold |
| 5,252,629 A | 10/1993 | Imai et al. |
| 5,256,447 A | 10/1993 | Oxman et al. |
| 5,264,485 A | 11/1993 | Müller et al. |
| 5,264,513 A | 11/1993 | Ikemura et al. |
| 5,273,574 A | 12/1993 | Arnold |
| 5,276,068 A | 1/1994 | Waknine |
| 5,306,338 A | 4/1994 | Tsunekawa |
| 5,382,284 A | 1/1995 | Arnold |
| 5,427,613 A | 6/1995 | Arnold |
| 5,534,562 A | 7/1996 | Jensen et al. |
| 5,554,030 A | 9/1996 | Ario et al. |
| 5,595,487 A | 1/1997 | Ario et al. |
| 5,662,886 A | 9/1997 | Oxman et al. |
| 5,708,052 A | 1/1998 | Fischer et al. |
| 5,844,018 A | 12/1998 | Jacobs et al. |
| 5,847,020 A | 12/1998 | Ibsen et al. |
| 5,849,813 A | 12/1998 | Oxman |
| 5,866,629 A | 2/1999 | Santerre et al. |
| 5,866,630 A | 2/1999 | Mitra et al. |
| 5,876,208 A | 3/1999 | Mitra et al. |
| 5,922,786 A | 7/1999 | Mitra et al. |
| 5,973,022 A | 10/1999 | Lu et al. |
| 5,975,906 A | 11/1999 | Knutson |
| 5,997,302 A | 12/1999 | Alpert |
| 6,004,390 A | 12/1999 | Pflug et al. |
| 6,127,450 A | 10/2000 | Angeletakis |
| 6,270,348 B1 | 8/2001 | Petersen |
| 6,274,644 B1 | 8/2001 | Pelerin |

FOREIGN PATENT DOCUMENTS

| | | |
|---|---|---|
| EP | 0 234 934 A2 | 2/1987 |
| WO | WO 96/31559 | 10/1996 |

Primary Examiner—James J. Seidleck
Assistant Examiner—Sanza L. McClendon
(74) Attorney, Agent, or Firm—Workman Nydegger

(57) ABSTRACT

Dental bonding compositions and methods for promoting adhesion of an amalgam-based restorative material to a dental substrate. The inventive compositions include one or more polymerizable resins that are able to adhere to a dental substrate when at least partially polymerized, one or more polymerization photoinitiators in an amount so as to result in partial polymerization of the resin when the compositions are irradiated with radiant energy, and one or more chemical initiators (e.g., benzoyl peroxide) that cause further polymerization of the resin when the composition is contacted with an amalgam restorative. A bonding composition applied to a dental substrate and irradiated with radiant energy is more polymerized in a region adjacent to the dental substrate, while a less polymerized inhibition layer forms in the region of the surface. Packing an uncured amalgam into the dental preparation mechanically disrupts the inhibition layer so as to form peaks, troughs and other irregularities. Upon curing the amalgam and bonding composition, the disrupted inhibition layer greatly enhances the overall bond between the amalgam, bonding composition, and dental substrate.

71 Claims, 4 Drawing Sheets

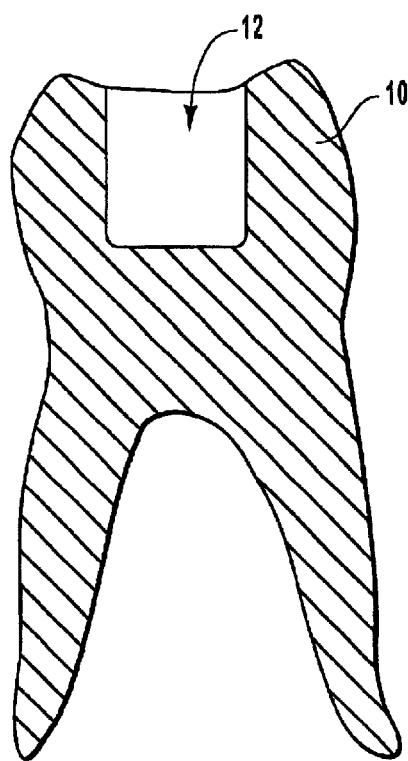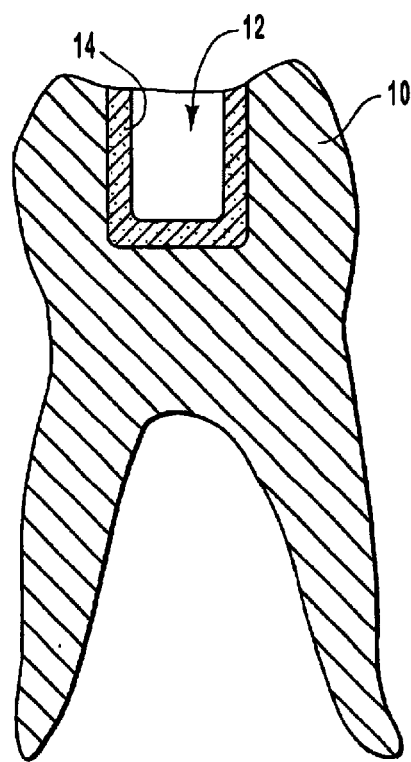
FIG. 1
FIG. 2
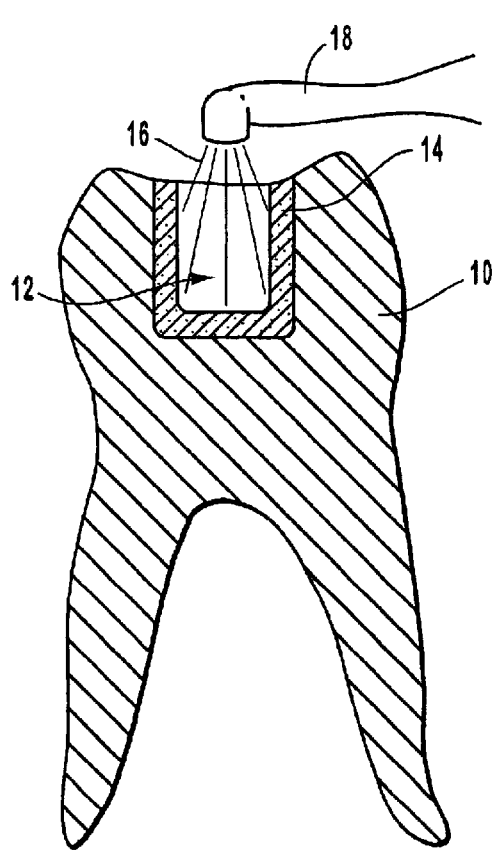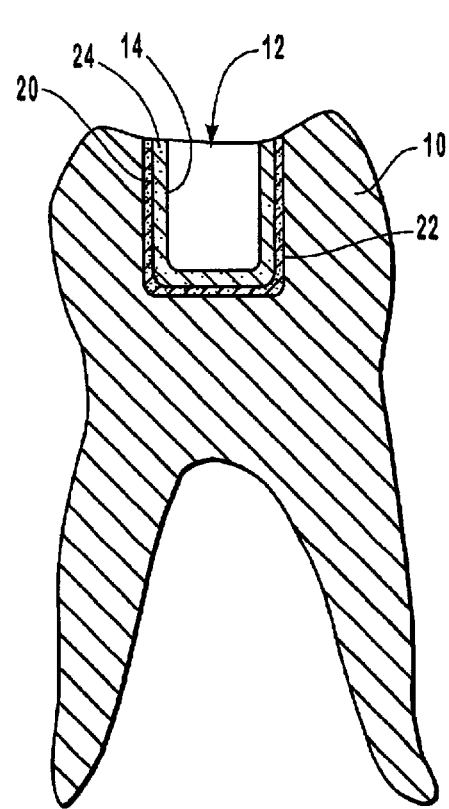
FIG. 3
FIG. 4

DENTAL BONDING COMPOSITIONS FOR ADHERING AMALGAM RESTORATIVES TO DENTAL SUBSTRATES

BACKGROUND OF THE INVENTION

1. The Field of the Invention

The invention is in the field of dental restoration compositions and methods, more particularly in the field of compositions and methods for bonding an amalgam restorative to a dental substrate. The bonding compositions are cured in steps to promote enhanced adhesion of the amalgam to the dental substrate.

2. The Relevant Technology

In the field of dental restorations, a variety of materials have been used to fill and restore cavities and other defects in a person's teeth. These include metals, such as gold, silver, platinum, alloy, and amalgams, curable polymers such as polyalkyl methacrylates, polycarbonates, cured products of polyfunctional vinyl monomers, composite resins comprising fillers and the aforementioned polymers, and ceramics such as porcelain. Because such materials do not readily adhere to dental tissues, the tooth, and in particular the pulp, should be sealed or capped in order for the tooth to remain vital and avoid being infected with bacteria.

Polymeric restoration materials such as composites, as opposed to metal-based restoration materials such as amalgam, are fairly compatible with bonding agents and adhesives. This quality allows composites and other polymeric restoration materials to be directly bonded to the teeth, thereby allowing such materials to be firmly and sealingly attached to the patient's tooth, regardless of the shape of the hollow or dental preparation formed in the tooth. This allows the dental practitioner to remove only so much of the decayed or damaged tooth as will prevent further damage or decay to the tooth once the dental preparation has been sealed and filled using a combination of the composite restoration material and bonding agent. In addition, composite restoratives can be formulated to match the color of the patient's teeth, thus resulting in a more cosmetically pleasing tooth restoration compared to amalgam or other metal restoratives, which typically assume the color of the metal or metals that make up the restorative.

Amalgams and other metal restoratives are generally incapable of forming a strong bond with dental substrates, even when used in combination with conventional adhesive bonding agents. Restoration techniques that involve the use of amalgam or other metal restoratives typically require the removal of much larger quantities of the dental substrate, as compared to composite restorative techniques, in order to provide for mechanical overhangs of dental tissue that mechanically retain the cured or hardened metal restoration material within the dental preparation. Thus, in contrast to restoring a tooth using a polymer-based restoration materials, the practitioner must not only remove the decayed or damaged portion of the tooth but also so much of the surrounding healthy and undamaged tooth as will result in a dental preparation of the proper shape for mechanically retaining the hardened or cured metal restoration material. In general, dental preparations suitable for receiving amalgam or other metal restoratives advantageously widen toward the interior of the tooth. In this way, the hardened or cured metal restorative is mechanically held in place by overhanging or converging dental tissues. Because there is no significant bond between the amalgam and the tooth, microleakage at the margins can occur.

Even though amalgams and other metal restoration materials are typically stronger and more durable than polymeric restoration materials, the use of amalgam and other metals generally results in a weaker, less durable restored tooth compared to a tooth restored using a composite restorative. Increased tooth weakness results from the necessity of removing substantially more of the tooth than simply the decayed portion and from the inability of the amalgam or other metal to strongly bond to the tooth. Preparing the tooth to receive the amalgam or other metal restorative results in a prepared tooth that is at once smaller in size and which contains a much larger weakening discontinuity or void therethrough compared to a tooth prepared to receive a polymeric restorative. In addition, the lack of any significant bond between the remaining dental tissue and the amalgam or other metal restorative results in much lower total composite strength of the finished tooth compared to a restored tooth in which the restorative and tooth form a strong composite bond.

In view of the advantages of composite restorative materials and techniques described herein, the use composites is rapidly increasing, at least in the United States, while the use of amalgams or other metal restoratives is generally declining. Nevertheless, there is still significant demand for amalgam restoratives. Many dentists have used amalgam restoratives for decades and are very skilled in the techniques used to prepare teeth to receive such restoratives. Dentistry, like other professions, is a skilled profession in which practitioners often opt to continue using procedures that they are comfortable with. Similarly, many patients who have had amalgam fillings all their lives are conservative and resistant to change simply because composites are new and possibly "high tech". As the common adage goes, "if it ain't broke, don't fix it."

Moreover, amalgam restoratives have certain advantages over composite restoratives, not the least of which is cost. Another is ease of use. Amalgam restoratives typically comprise a mixture of relatively inexpensive metals (e.g., mercury, silver, copper and tin) that, when mixed together, are initially pliable and packable but which quickly cure or harden into a durable tooth filling as the metals react and become compounded. Examples of commonly-used amalgam restorative materials include TYTIN, which is manufactured and sold by Kerr Corporation, located in Orange, Calif., and VALIANT PH.D., which is distributed in the United States by Vivadent/Ivoclar North America, located in Amherst, N.Y. In contrast, composite restoratives typically include polymerizable resins, fillers, adhesives, and curing agents which, in the aggregate, are many times more expensive than amalgam restoratives. Whereas the cost differential may not matter to the wealthy or vain who will pay anything for stronger and/or more cosmetically appealing teeth, it does matter to many, particularly individuals on limited budgets and in less affluent countries.

Another problem with composite restoratives is that they are subject to greater variability in quality and strength compared to amalgam restoratives. Their use also requires more technical skill. When polymers cure they tend to shrink, and polymerization shrinkage is a problem that is generally dealt with by technique rather than by formulation. Technique is a learned trait, and a dentist with poor technique can improperly bond the composite to the patient's tooth. A composite restorative that is not adequately bonded to the tooth, i.e., that is partially detached, can provide ingress of bacteria into the dentine or pulp. Such restorations should be repaired by removing and replacing the improperly bonded composite material. Worse, improper placement of a shrinkable composite within a fragile tooth can cause it to crack or fracture, thus requiring major dental repair such as a crown.

In view of the foregoing, the choice between whether to use composite restoratives, on the one hand, or amalgam restoratives, on the other, to repair a decayed or damaged tooth comes down to weighing the respective advantages and disadvantages of each and then determining which are most important to the dental practitioner and/or the patient. When properly placed, the use of composite restoratives generally result in a much better composite bond with the tooth and a more cosmetically pleasing look. On the other hand, amalgam restoratives provide greater simplicity of use and much lower cost. For this reason, restorations involving a child's "baby" (or milk) teeth are performed using amalgam, since such restorations are, by definition, only temporary. Nevertheless, as stated above, amalgam restoratives are unable to form strong bonds with dental substrates such that the dental preparation must be large enough and properly shaped in order to provide for mechanical retention of the hardened amalgam.

Some attempts have been made to bond amalgam to dentin and other dental tissues, but with little success at yielding a commercially viable or professionally acceptable solution. Hence, the vast majority of dental restorations involving the use of amalgam restoratives are performed without the use of an adhesive bonding agent.

In view of the foregoing, it would be an advancement in the art of dental restorations to provide adhesive compositions and methods that provided for strong and reliable bonding between amalgam restorative materials and dental substrates. It would be a further advancement if such adhesive compositions and methods were able to seal the underlying dental substrate, as well as provide an improved seal between the amalgam restorative and the dental substrate.

Such compositions and methods for adhering an amalgam-based restorative material to a dental substrate are disclosed and claimed herein.

SUMMARY OF THE INVENTION

The present invention encompasses greatly improved bonding compositions and methods for restoring a patient's tooth using an amalgam restorative material. More particularly, the compositions and methods according to the invention allow the dental practitioner to form a much stronger bond between a dental substrate and an amalgam restorative material. This, in turn, yields a stronger and more durable tooth restoration compared to conventional amalgam-based restorations due to greatly increased composite strength. In some cases, the dental practitioner may be able to remove less dental material from the decayed or damaged tooth that would be otherwise be required if mechanical retention were the only force holding the tooth and the amalgam restoration together. Keeping more of the original tooth intact will generally preserve more of its strength and reduce the risk of subsequent breakage or cracking of the restored tooth. Such compositions and methods also advantageously seal the underlying dental substrate, including the dentin tubules, and result in a substantially better seal between the substrate and amalgam, either of which would be expected to reduce tooth sensitivity and the propensity of the tooth to become decayed in the future. Such bonding greatly reduces or eliminates microleakage at the margins.

The amalgam bonding compositions according to the invention are formulated so as cure or harden in steps. In particular, they are formulated to only partially cure within the dental preparation prior to packing the amalgam into the dental preparation. The partially cured bonding composition remains pliable and deformable, particularly at the surface, for reasons that will be discussed more fully below. This permits the upper layer of the bonding composition to become physically disrupted when packing the amalgam within the dental preparation, which substantially increases the mechanical interaction and interface area between the bonding composition and the amalgam. After the amalgam restorative material and bonding composition have both been cured, this physical disruption of the upper layer of the bonding composition and resulting increased mechanical interaction and interface area between the two results in greatly increased bond strength and adhesion between the bonding composition, amalgam restorative, and the dental substrate.

The bonding compositions according to the invention preferably include at least one polymerizable material, a first polymerization initiator that allows the dental practitioner to partially polymerize or cure the polymerizable material within the dental preparation prior to packing the uncured amalgam restoration material therewithin, and a second polymerization initiator that causes the polymerizable material to continue to polymerize or cure beneath the packed amalgam restoration material. These work together to form a strong bond between the amalgam, bonding agent, and dental substrate. The inventive bonding compositions may include fillers, active agents, adjuvents and other additives as desired in addition to the components specifically identified herein. They may be one-part or multi-part bonding systems.

The polymerizable material may include one or more polymerizable promoters, such as methacrylic acid or derivatives thereof. In addition to, or instead of the polymerizable promoter, the polymerizable material may include one or more polymerizable resins, such as 2-hydroxyethyl methacrylate (HEMA) or bis glycerol methacrylate phosphate. One of ordinary skill will readily understood, when reading the present disclosure, that any appropriate polymerizable material may be used so long as the resulting bonding composition has desired properties and provides desired bonding characteristics between the dental substrate and amalgam restorative.

The first polymerization initiator preferably comprises at least one photoinitiator, examples of which include phosphine oxide, phenyl bis(2,4,6-trimethyl benzoyl); 2-hydroxy-2-methyl-1-phenyl-1-propanone; and camphoroquinone. The identity and concentration of the first polymerization initiator are selected so that the polymerizable material within the bonding composition is only partially polymerized upon placing the bonding composition within a dental preparation and irradiating the composition with radiant energy. Because the aforementioned photoinitiators are consumed during polymerization, i.e., they are reactants rather than catalysts, their concentration can be selected so as to result in a desired degree of partial polymerization. Thus, if an amount X of the photoinitiator is required to fully polymerize an amount Y of the polymerizable material, including a quantity of the photoinitiator that is less than X would be expected to result in only partial polymerization or curing of the polymerizable material. One of ordinary skill in the art will, through routine testing, be able select an appropriate quantity of photoinitiator that will result in a desired level of partial polymerization of a given quantity of polymerizable material. In this way, the level or degree of partial polymerization can be controlled.

The second polymerization initiator preferably comprises at least one chemical initiator that is able to cause the polymerizable material to continue to polymerize or cure after placement of the amalgam restorative within the dental preparation. Because amalgam restoratives are opaque, they generally do not permit further polymerization of the underlying bonding composition by photoinitiation, i.e., they substantially or entirely shield the bonding composition from all light that may be emitted by a dental curing light. For this reason, the second polymerization initiator will typically be a chemical initiator that causes polymerization of the polymerizable material in the absence of radiant energy. An example of an appropriate chemical initiator is benzoyl peroxide. The second polymerization initiator not only causes the polymerizable material to more completely or entirely polymerize, it also allows the dental practitioner to time the curing or hardening of the bonding agent so that it remains pliable while packing the amalgam into the dental preparation and then cures into a hardened and less-pliable material after the amalgam has been packed.

One of ordinary skill will readily appreciate that timing of the extent of final cure of the bonding agent may be carried in any desired manner. In a preferred embodiment, the amalgam itself can be used to trigger the final curing or polymerization of the polymerizable material within the bonding agent. Benzoyl peroxide is relatively stable in the presence of many polymerizable materials and photoinitiators, even after partially polymerizing the polymerizable material by irradiation with radiant energy from a dental curing light. This allows the chemical curing process to be controlled or prevented prior to packing the amalgam. In some cases, the benzoyl peroxide is sufficiently stable such that the bonding composition can be premixed as a stable, one-part composition. Keeping the one-part composition from overheating helps to prevent it from prematurely polymerizing. However, when the bonding composition comes into contact with the amalgam restorative, particularly when the upper layer of the partially cured composition is disrupted and agitated during packing of the amalgam restorative into the dental preparation, the interaction of metal within the amalgam and the benzoyl peroxide causes the benzoyl peroxide to decompose. This, in turn, causes the polymerizable material to further polymerize so as to cause the bonding agent to harden or cure. Such interaction may involve a catalytic reaction, heat or both.

Without being limited to any particular theory, it is believed that exposure of the bonding agent to air inhibits polymerization of the polymerizable material. As a result, after the bonding agent has been applied to a dental substrate and then exposed to radiant energy (e.g., from a dental curing light) to induce partial polymerization of the polymerizable material, the region of the bonding agent that is shielded from the air is preferentially cured or hardened compared to the region that is exposed to the air. Thus, when partially curing the bonding agent with the curing light, the underlying region or layer of the bonding agent adjacent to the dental substrate is preferentially cured or hardened, while the upper region or layer of the bonding agent at the exposed surface forms an "inhibition layer" (or "inhibited layer") of less cured or hardened bonding agent. This differential in curing provides the benefit of allowing the upper surface layer to remain pliable and easily deformable so that, when the amalgam restorative is packed into the dental preparation, the upper portion of the bonding agent can beneficially become disrupted and agitated so as to increase the interface area and mechanical interaction between the bonding agent and amalgam. On the other hand, the more fully cured or hardened bonding agent adjacent to the dental substrate strengthens the bond between the bonding agent and the dental substrate. This helps to prevent separation of the bonding agent from the dental substrate while packing the amalgam into the dental preparation.

After the amalgam has been packed into the dental preparation and placed over the bonding agent, the chemical initiator causes the polymerizable material within the bonding agent to continue curing and hardening, including the initially less cured inhibition layer. In the case of benzoyl peroxide, it is believed that this additional polymerization is triggered by some interaction between the benzoyl peroxide and the amalgam that causes the benzoyl peroxide to decompose and catalyze further polymerization. Shielding of the bonding agent from air by the packed amalgam restorative facilitates curing as the air that formerly inhibited polymerization is displaced from within the filled tooth by the amalgam.

In a preferred method of restoring a tooth, the decayed or damaged portion of the tooth is removed, together with additional dental tissue as necessary to form an appropriate dental preparation or hollow. In many cases, it will be possible for the dental preparation to be significantly smaller than conventional dental preparations used in conventional amalgam restoration procedures, e.g., formed without overhanging dental tissue designed to mechanically retain the amalgam within the dental preparation, as is generally required using convention amalgam restoration methods. The dental preparation is preferably conditioned with an aqueous acid solution, such as a 35% phosphoric solution, in order to etch the enamel and/or remove the smear layer that typically forms when removing dentin by drilling or abrading. Thereafter, the dental preparation is preferably washed with water to remove the acid and any dissolved minerals and loose, detached dentinal materials. After conditioning and washing, the tooth surface may be dried with pressurized air and/or suction.

The conditioned, washed and dried dental preparation is then preferably coated with an amalgam bonding composition according to the invention. In particular, the bottom, sides and any other surface of the dental preparation that will contact the amalgam restorative is coated with the bonding composition. The bonding composition is then partially cured or polymerized. This is preferably accomplished by light curing a composition that has been formulated to include enough photoinitiator to only partially cure the composition to a desired extent, e.g., so as to cause the layer of bonding composition adjacent to the dental substrate to preferentially cure sufficiently so as to form a bond between the dental substrate and the bonding composition, while leaving the exposed upper layer less cured and more pliable. This is the so-called "inhibition" or "inhibited" layer. In alternative embodiments, the degree of polymerization may be controlled in other ways, such as by irradiating the bonding composition for less time than is necessary for it to more completely cure, or by including a slow acting chemical initiator (e.g., in a two-part system).

After the bonding agent has been partially cured so as to form a bond with the dental substrate, while remaining pliable or deformable in the region of the exposed surface, an appropriate uncured amalgam restorative material is packed (or "condensed") into the dental preparation. The amalgam is packed into the dental preparation using conventional packing tools known in the art. As the packing tool pushes the amalgam into the dental preparation, typically with short, but firm, downward thrusts toward and through the amalgam, the deformable upper region of the bonding composition is deformed and disrupted, thereby causing troughs, peaks, and other significant irregularities to form in the surface of the bonding composition. Fingers of the deformable bonding agent can extend into the uncured amalgam so as to form roots therein. The pliable, uncured amalgam restoration material displaces the air and assumes a conformation that is complementary to the irregularities in the disrupted bonding composition. This greatly increases the mechanical interaction between the bonding layer and the amalgam. On the other hand, the region of the bonding agent adjacent to the dental substrate is preferably sufficiently cured so as to resist deformation and detachment from the dental substrate.

Once the amalgam has been packed and shaped, it is allowed to cure. Conventional amalgams cure over time after initially mixing the initially separate metals together. Over time, the metals react and become bonded, which causes the amalgam restoration material to become hardened. At the same time, the amalgam also preferably causes one or more chemical initiators to begin the final polymerization of the polymerizable material in order to finally cure or harden the bonding agent. Whereas the two curing reactions may coincide to some extent, they may differ in duration. In alternative embodiments, one or more chemical curing agents can be selected, stored separately, and then mixed with the other components of the bonding composition in order to trigger the second curing step independently from contacting the amalgam with the bonding agent.

The various embodiments of the bonding compositions and methods according to the invention provide a number of advantages over the prior art. For example, the increase in bond strength between the dental substrate and amalgam restorative provides for greater composite action between the tooth and the amalgam. Reliable bond strengths between about 25–37 MPa have been achieved when using the most preferred compositions and methods described herein. This should, in and of itself, yield a stronger restored tooth. Moreover, greatly increasing the bond strength between the amalgam restorative and the dental substrate should, at least in theory, reduce or eliminate the need for mechanical retention of the amalgam restorative within the dental restoration. This would potentially allow the dental practitioner to remove significantly less tooth material when forming a dental preparation for filling with an amalgam restorative. Improving the bond between amalgam restorative materials and dental substrates would also be expected to improve the seal between the amalgam restorative and the tooth, thereby greatly reducing the chance that bacteria could enter and fester within gaps or fissures between the amalgam and the tooth.

These and other features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 1 is a side cross-section view of a tooth that include a dental preparation formed therein for receipt of a restorative;

FIG. 2 is a side cross-section view of the tooth of FIG. 1 in which the dental preparation has been coated with a dental bonding composition;

FIG. 3 is a side cross-section view of the tooth of FIG. 2 in which the dental bonding composition within the dental preparation is being irradiated with radiant energy in order to partially cure the bonding composition;

FIG. 4 is a side cross-section view of the tooth of FIG. 3 in which the partially cured dental bonding composition is more fully cured in the inner region or layer adjacent the surface of the dental preparation and less cured in the exposed outer region or layer;

DETAILED DESCRIPTION OF THE PREFERRED EMBODIMENTS

Figure 5:
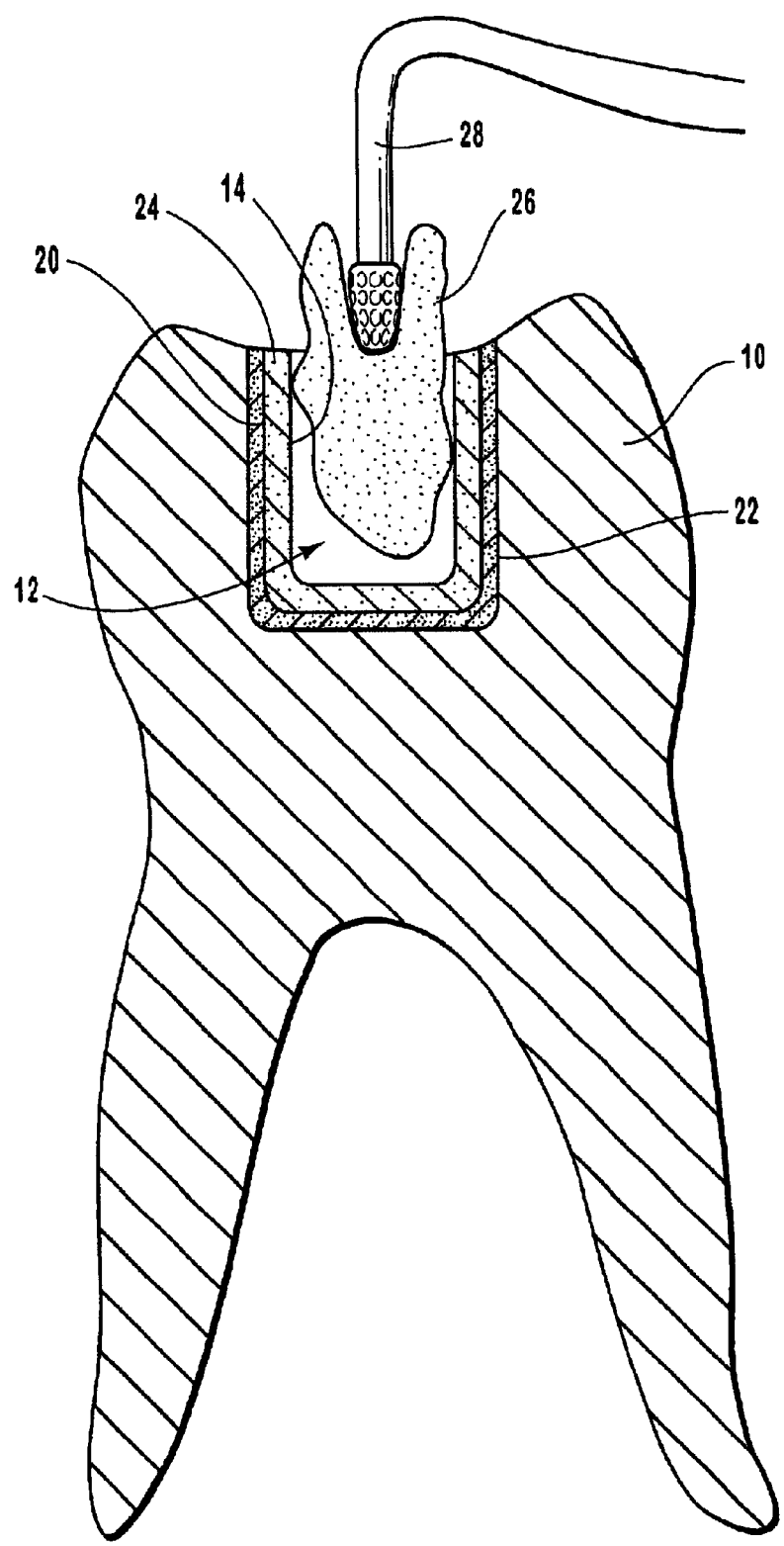
FIG. 5 is a side cross-section view of the tooth of FIG. 4 in which an uncured amalgam restorative material has been positioned partially within the dental preparation prior to packing against the outer layer of the bonding composition.

I. Introduction and Definitions.

The present invention encompasses compositions and methods for use in restoring a patient's tooth using an amalgam or other metal restorative. More particularly, the compositions and methods result in the formation of an actual bond between a dental substrate and the metal restorative. Such bonds yield stronger, more durable tooth restorations because of greatly increased composite strength between the amalgam and tooth and because more of the tooth can be left intact during formation of the dental preparation in many cases. In addition, the dental bonding compositions are also useful in sealing the dental substrate, particularly the dentin tubules, which protects the tooth from further infection and decay. They also prevent or inhibit microleakage at the margins between the tooth and amalgam.

The amalgam bonding compositions according to the invention are formulated to only partially cure within the dental preparation prior to packing the amalgam into the dental preparation so as to remain pliable and deformable at the surface. When packing the amalgam within the dental preparation, the deformable bonding composition becomes disrupted to include troughs, peaks, fingers that extend into the amalgam, and other irregularities that substantially increase the mechanical interaction and the strength of the resulting bond between the bonding composition and the amalgam.

Preferred dental bonding compositions according to the invention include at least one polymerizable material, a first polymerization initiator that causes the polymerizable material to only partially cure or harden prior to packing (or condensing) the uncured amalgam restoration material into the dental preparation, and a second polymerization initiator that causes the polymerizable material to continue to cure beneath the packed amalgam restoration material. The inventive bonding compositions may include fillers, adjuvents, active agents, or other additives as desired in addition to the components specifically identified herein.

The term "dental substrate", as used in the specification and the appended claims, broadly refers to a tooth, any portion thereof, or a prosthetic related to the tooth. Examples of "dental substrates" include, but are not limited to, tooth enamel, dentin, other structures of a tooth, metal crowns or fillings, porcelain crowns or overlays, composite fillings or crowns, other dental prosthetics, and other structures and materials related to the repair and reconditioning of teeth.

The term "dental preparation", as used in the specification and the appended claims, broadly refers to any void, depression, hollow, indentation, crevice, crack, or any other irregularity that can be filled with a restorative material. Examples include, but are not limited to, void spaces that are formed by removing dental tissue using, e.g., a dental cutting, grinding, or abrading tool. It may also include extreme, but natural irregularities.

The term "restorative", as used in the specification and the appended claims, broadly refers to any filling or restoration material used to fill a "dental preparation". Examples include, but are not limited to, composite resins (e.g., packables, pastes and flowables), amalgam metals, other metals, and porcelain.

The term "partially cured", as used in the specification and the appended claims, refers to a condition or state of a dental bonding composition in which one or more polymerizable materials contained therein have become partially polymerized. That is, they are still capable of further polymerization to yield a harder, less pliable material (i.e., they remain at least partially "unpolymerized".

The term "cured", as used in the specification and the appended claims, refers to a dental bonding composition that has been sufficiently polymerized so as to be sufficiently hardened and non-pliable so that it can form a reasonably strong bond between an amalgam or other restorative and a dental substrate. Thus, though a completely polymerized bonding composition represents an example of a "cured" material, a bonding composition that is substantially polymerized so as to yield sufficient bond strength, even if it is capable of some further polymerization, may still be considered to be "cured".

The terms "harden" and "hardened", as used in the specification and the appended claims, refers to a level of polymerization or curing of a dental bonding composition or amalgam restorative such that they are not readily deformable and so that the bond between the "hardened" bonding composition and the "hardened" amalgam restorative has achieved a substantial portion (i.e. greater than a majority of) its final bond strength.

The term "uncured", as used in the specification and the appended claims, refers to a condition in which a dental bonding composition is readily flowable onto a dental substrate and a condition in which an amalgam restorative is readily packable within a dental preparation, regardless of whether some incidental partial curing of the bonding composition or amalgam has taken place.

The term "oligomer", as used in the specification and the appended claims, shall include dimers, trimers, tetramers, and other prepolymers derived from one or more monomers.

II. Preferred Dental Bonding Compositions.

The preferred dental bonding compositions according to the present invention comprises at least one polymerizable material and at least one polymerization initiator. More preferred compositions included two different types of polymerization initiators in order to more easily facilitate the step-wise or progressive curing of the bonding agent. Such bonding compositions may also include one or more solvents, fillers, natural resins, fluoride-releasing agents, and other adjuvents and additives as desired. They may be one-part or multi-part systems.

A. Polymerizable Materials.

Any polymerizable material that is capable of curing and adhering to a dental substrate may be used within the dental bonding compositions according to the invention. The bonding compositions preferably include one or more polymerizable materials chosen from one or both of two classes of polymerizable materials designated as "polymerizable promoters" and "polymerizable resins".

1. Polymerizable Promoters

The term "polymerizable promoter", as used in the specification and the appended claims, refers to a class of polymerizable monomers, oligomers or other prepolymers that include at least one ethylenically unsaturated group and at least one carboxylic acid group. As a result of including a carboxylic acid group, polymerization promoters are hydrophilic, which makes them very compatible with highly mineralized and polar dental tissues. The polymerizable promoter is capable of being polymerized in situ by means of the one or more polymerization initiators. In the preferred methods according to the invention, this will occur after the bonding composition has been placed within the dental preparation.

The polymerizable promoter may be included in the dental bonding composition in a broad range from about 0.05% to about 99.95% by weight of the bonding composition. The polymerizable promoter is preferably included in a range from about 0.5% to about 60% by weight of the bonding composition, more preferably in a range from about 0.75% to about 50% by weight, and most preferably in a range from about 1% to about 40% by weight of the bonding composition.

In general, preferred polymerizable promoters within the scope of the present invention have the following formula:

wherein R is a hydrogen radical, a methyl group, a saturated aliphatic radical, an unsaturated aliphatic radical, a halogen radical or a CN radical.

Examples of polymerizable promoters having the aforementioned chemical formula include, but are not limited to, methacrylic acid, acrylic acid (also known as 2-methyl-2-propanoic acid and 2-propanoic acid, respectively), mixtures of the foregoing and derivatives of the foregoing. Such compounds are highly polar and generally able to form strong adhesive bonds with dental substrates, particularly dentin and enamel.

Polymerizable promoters within the scope of the present invention can also have the following formula:

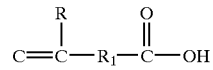

wherein R is a hydrogen radical, a methyl group, a saturated aliphatic radical, an unsaturated aliphatic radical, a halogen radical or a CN radical; and wherein $R_1$ is at least one oxygen radical, a saturated aliphatic radical, a saturated aliphatic radical interrupted by at least one oxygen or other polar radical, an unsaturated aliphatic radical, an unsaturated aliphatic radical interrupted by at least one oxygen or other polar radical, a homocyclic radical, a heterocyclic radical, a polymerizable moiety, or an aryl radical having four to six carbon atoms and a valency of n+1, with n being an integer of at least 6.

Examples of the aforementioned polymerizable promoters include, but are not limited to, 4-pentenoic acid, 6-heptenoic acid, 2,2-dimethyl-4-pentenoic acid, mixtures of the foregoing, and derivatives of the foregoing. Of course, where $R_1$ is a chemical bond, the polymerization promoter has the general formula:

2. Polymerizable Resins

The term "polymerizable resin", as used in the specification and the appended claims, refers to a either a hydrophilic polymerizable compound with at least one hydroxyl group, a hydrophobic polymerizable alkyl, or a polymerizable compound having at least one hydrophobic moiety and at least one hydrophilic moiety. Polymerizable resins within the scope of the present invention, include but are not limited to, hydroxyalkyl methacrylates, hydroxyalkyl acrylates, alkyl methacrylates, alkyl acrylates, mixtures of the foregoing, derivatives of the foregoing and the like. More specific examples of polymerizable resins within the scope of the invention include, but are not limited to, 2-hydroxyethyl methacrylate (HEMA), bis glycerol methacrylate phosphate, bisphenol-A-glycidyl methacrylate (Bis-GMA), glycerol dimethacrylate, methyl acrylate, methyl methacrylate, triethylene glycol dimethacrylate, mixtures of the foregoing, derivatives of the foregoing, and the like. Hydrophilic resins such as HEMA are particularly useful because the dentin contains significant mineral content and moisture, which results in better adhesion between the dentin and the bonding composition.

Polymerizable resins within the scope of the present invention may also include at least one amino group, at least one phosphate group, at least one phosphoric acid group or derivative, or at least one phosphorus acid group or derivative.

A preferred alkyl methacrylate substituted with a phosphoric acid derivative is bis glycerol methacrylate phosphate. Examples of other preferred alkyl methacrylates substituted with phosphoric acid or a phosphoric acid derivative include: bis 2-hydroxy ethyl methacrylate phosphate, phosphate ester of p-hydroxyphenyl methacrylamide, phosphate ester of 3-hydroxy propyl methacrylate, and phosphate ester of 4-hydroxy butyl methacrylate. In general, it is within the scope of the invention to utilize polymerizable resins that include one or more of the following phosphoric acid or phosphorous acid radicals or derivatives:

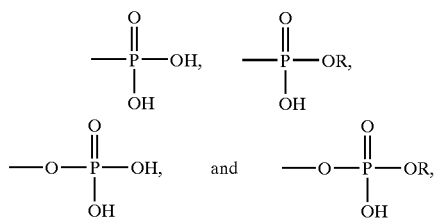

wherein R is an alkyl.

The polymerizable resins may be included in the dental bonding compositions in a broad range from about 0.05% to about 95% by weight of the bonding composition. The polymerizable resin is preferably included in an amount in a range from about 0.5% to about 60% by weight of the bonding composition, more preferably in a range from about 0.75% to about 50% by weight, and most preferably in a range from about 1% to about 40% by weight of the bonding composition.

Even though hydrophobic polymerizable resins such as Bis-GMA may be included within the compositions according to the invention, it is preferable to include less of such resins than the amount of hydrophilic polymerizable resin, or combined hydrophilic resin and polymerizable promotor in the case where both are included.

On the one hand, Bis-GMA is a useful resin because it contains hydrophilic end groups in addition to the main hydrophobic groups or moieties contained therein. Bis-GMA also hardens into a very durable material when cured. On the other hand, it has been found that including too much Bis-GMA yields a bonding composition having reduced bonding strength when used to adhere or bond amalgam to a dental substrate. Without being bound by any particular theory, it has been posited that the highest bond strengths are obtained when the final cured bonding composition remains somewhat flexible, resilient and less brittle. Accordingly, when it is desired to include Bis-GMA to increase the hardness and durability of the bonding compositions within the scope of the invention, and even though bonding compositions according to the invention may include any desired quantity of Bis-GMA, Bis-GMA is preferably included in an amount of less than about 4% by weight of the bonding composition, more preferably less than about 3% by weight, and most preferably less than about 2% by weight of the bonding composition.

This is a surprising and unexpected result because one of ordinary skill in the art would expect the largely mechanical bond between the bonding composition and the amalgam restorative to increase with increased hardness on the part of the bonding composition when cured. Instead, bond strengths were found to actually increase as the concentration of Bis-GMA was reduced, or eliminated altogether, compared to a formulation that included 5% Bis-GMA.

B. Initiators.

It is within the scope of the invention to use one or more initiators selected from the group consisting of photoinitiators and chemical initiators.

1. Photoinitiators.

The term "photoinitiator", as used in the specification and appended claims, refers to any compound or blend of compounds that cause a polymerizable materials to at least partially polymerize through irradiation of the initiator with radiant (e.g., light) energy. Exemplary photoinitiators include, but are not limited to, α-diketones; camphoroquinone; phenyl bis (2,4,6-trimethyl benzoyl) phosphine oxide; 2-hydroxy-2-methyl-1-phenyl-1-propanone; benzoin methyl ether; benzophenone; and 9,10-anthraquinone. The photoinitiators can be used with or without tertiary amines.

Tertiary amines are relatively stable when mixed with photoinitiators, and can be used to accelerate photoactivated cross-linking. Thus, tertiary amines can be used to augment the effect of a photoinitiator without causing the mixture to become unstable prior to light activation. Hence, when used with a photoinitiator, tertiary amines form part of the photo-initiation system. Example of tertiary amines that may be used in the inventive compositions include, but are not limited to, dimethylamino ethylmethacrylate, triethylamine; 2-dimethylamino ethanol; diethylaminoethyl methacrylate; trihexyl amine; N,N-dimethyl-p-toluidine; N-methylethanolamine; and 2,2-(p-tolylamino)-diethanol.

The photoinitiators are advantageously included in selected amounts in order to control the extent or degree of polymerization or curing of the dental bonding compositions according to the invention. Photoinitiators are typically reactants, i.e., they are consumed in the polymerization reaction, rather than being catalysts, which are continuously regenerated and not consumed during polymerization. Thus, it is possible to restrict the amount of photoinitiator so as to deliberately under-polymerize the bonding composition prior to packing or condensing an amalgam into the dental preparation. By knowing the ratio of molar equivalents that is required for a particular photoinitiator to cause a given quantity of polymerizable material to fully polymerize, and in view of the principles and concepts disclosed herein, one of ordinary skill in the art will be able to design a composition having a desired degree of partial polymerization or curing. Similarly, after gaining an appreciation for the principles and concepts disclosed herein, one of ordinary skill will be able, through routine trial and error testing, to determine an optimal concentration of a particular photoinitiator that will result in a desired level of partial polymerization of a given polymerizable material upon exposing the composition to an excess of radiant energy.

The extent of partial polymerization of the bonding composition is further inhibited when exposed to air, since oxygen generally inhibits polymerization. Thus, when a layer of the dental bonding composition is applied to a dental preparation and then partially polymerized, the sublayer or portion of the bonding composition next to the dental substrate is polymerized to a greater extent than the outer sublayer or portion that is exposed to air, which forms an "inhibition" or "inhibited" layer. In some cases, rather than distinct layers, there may be a gradient of increasing polymerization from the exposed surface of the bonding composition to the inner surface adjacent to the dental substrate. This differential in the extent of partial polymerization is advantageous because it allows the surface layer to remain sufficiently pliable and deformable such that troughs, peaks and other irregularities can be readily formed therein upon packing an uncured amalgam restorative within the dental preparation. Moreover, the more fully-cured layer or portion of the bonding composition adjacent to the dental preparation surface helps to prevent inadvertent dislodging or separation of the bonding composition from the dental substrate.

It will be readily appreciated that the desired under-polymerization of the dental bonding composition used to bond an amalgam to a dental substrate can be controlled in other ways. Accordingly, in preferred methods according to the invention, it may be possible to under-polymerize a bonding composition by restricting the amount of radiant energy that is applied to the bonding composition (i.e., by restricting the intensity and/or duration of the radiant energy). Thus, whereas preferred dental bonding compositions according to the invention include a stoichiometrically insufficient amount of photoinitiator to effect under-polymerization of the composition even when exposed to an excess of radiant energy, preferred methods according to the invention may be carried out using both the preferred compositions described herein as well as compositions that include a stoichiometrically sufficient amount of photoinitiator that are under-polymerized using a deficiency of radiant energy.

The amount of polymerization photoinitiator to be included within the preferred dental bonding composition according to the invention is generally dependent on the identity and concentration of the polymerizable portion, as well as the level of partially polymerization that is desired. In order to restrict the extent of polymerization, the photoinitiator will preferably be included in an amount in range from about 0.001% to about 0.5% by weight of the dental bonding composition, more preferably in a range from about 0.005% to about 0.2%, and most preferably in a range from about 0.008% to about 0.08% by weight of the dental bonding composition.

2. Chemical Initiators.

The term "chemical initiator", as used in the specification and appended claims, refers to any compound or blend of compounds that cause a polymerizable material to at least partially polymerize as a result of a chemical reaction between the chemical initiator (or a decomposition product thereof) and the polymerizable material, without the use of radiant energy. Examples of chemical initiators within the scope of the invention include a wide variety of compounds that are sufficiently unstable that they can decompose into radicals capable of catalyzing or otherwise causing the polymerization of the polymerizable material.

Specific examples of radical-forming substances include the large class of compounds known as peroxides, more specifically including, but not limited to, benzoyl peroxide, 2-butanone peroxide, lauroyl peroxide, and tert-butyl peroxide. Benzoyl peroxide is preferred because it is soluble and relatively stable when mixed with the polymerizable materials disclosed herein as long as the composition is substantially free of errant metals or metal ions that trigger the decomposition of benzoyl peroxide. In addition, benzoyl peroxide remains relatively stable when kept at or below room temperature. In the case where the dental bonding compositions according to the invention are formulated as stable, one-part compositions, such compositions are advantageously maintained below the decomposition temperature of benzoyl peroxide in order to prevent premature polymerization and curing of the polymerizable material.

The amount of benzoyl peroxide or other chemical initiator that should be included with the dental bonding compositions according to the invention is somewhat dependent on the concentration of the polymerizable material. Nevertheless, because the interaction between benzoyl peroxide (particularly its decomposition products) and the polymerizable material is believed to be more catalytic in nature, including more or less benzoyl peroxide is believed to have a greater effect on the rate, rather than the extent, of final curing or polymerization of the bonding composition. The fact that benzoyl peroxide and other peroxides tend to be unstable in the presence of metals or metal ions makes them well-suited for use with amalgam or other metal restoratives.

Benzoyl peroxide remains sufficiently stable even after the bonding composition has been partially cured, e.g., by means of light-curing prior to packing the amalgam or other metal restorative within the dental preparation. Thereafter, the interaction between the amalgam or other metal restorative triggers the decomposition of the benzoyl peroxide or other peroxide which, in turn, catalyzes further polymerization of the polymerizable material within the dental bonding composition, including the inhibited layer. In this way, the final curing stage of the dental bonding composition can be timed so as to occur after the amalgam or other metal restorative has been packed into the dental preparation. In addition, the act of packing of amalgam or other metal restorative into the dental preparation displaces the oxygen therefrom, which further facilitates further curing of the inhibition layer by the chemical initiator.

In the case of a multi-part bonding dental bonding composition, it may be possible to include an amount of a chemical initiator that will cause the bonding composition, when mixed, to slowly cure over a predetermined amount of time. In this way, a dental practitioner can mix up a quantity of the multi-part (e.g., two-part) composition just prior to application to a dental preparation. After a set amount of time, when the bonding composition has been partially polymerized or cured to a desired degree, the amalgam can be packed into the dental preparation. As before, an upper inhibition layer should be significantly less cured than the inner sublayer adjacent to the dental substrate, which allows the upper layer to more easily form peaks, troughs and other irregularities when packing an uncured amalgam into a dental preparation. After packing the amalgam into the dental preparation, the bonding composition, including the inhibited layer, will continue to cure because of the chemical initiator. Packing the amalgam within the dental preparation will also displace the oxygen therefrom, thereby facilitating the further polymerization of the inhibition layer by the chemical curing agent. It may also serve to further accelerate polymerization by catalyzing accelerated decomposition of the chemical initiator.

Although tertiary amines such as dimethylamino ethylmethacrylate are relatively stable when mixed with photoinitiators, they are generally unstable in the presence of chemical initiators (e.g., benzoyl peroxide). Because of this, tertiary amines can be advantageously mixed with a bonding composition that includes a chemical initiator in order to activate or accelerate polymerization and curing of the bonding composition. In this way, tertiary amines can augment the effect of the chemical initiator. Hence, when used with a chemical initiator, tertiary amines form part of the chemical initiation system.

In general, benzoyl peroxide or other chemical initiators may be included in any appropriate amount, preferably in a range from about 0.001% to about 5% by weight of the dental bonding composition, more preferably in a range from about 0.01% to about 3% by weight, and most preferably in a range from about 0.1% to about 2% by weight of the dental bonding composition.

C. Natural Resins.

The bonding compositions may optionally include one or more natural resins. The term "natural resin", as used in the specification and the appended claims, includes a variety of substances that are found in natural sources such as trees, shrubs, plants or seeds. Natural resins within the scope of the present invention may be either polymerizable or non-polymerizable. If polymerizable, a natural resin may comprise a portion of the "polymerizable material". While the natural resins disclosed herein are chemicals that are found in, or can be obtained from, natural sources, the natural resins used with the present invention are not necessarily unaltered from their natural condition. Accordingly, the term "natural resins" shall also refer to derivatives of natural resins.

Suitable natural resins include, but are not limited to, rosins, distillates, saps, oils, balsams, and gums. More specific examples of useful natural resins include, but are not limited to, Canadian balsam, sandarac, mastic, pontianak, copal, manilla, peruvian, benzoin, elemi, opopanax, olibanum, styrax, benzoin siam, tolu, resinoid, tall, pine, eugenol, and the like.

Many natural resins comprise a mixture of chemicals. For example, Canadian balsam typically comprises 27.5% volatiles, such as pinene, nopinene, and β-phellandrene, 44.5% resin acid including 13% abietic and 8% neoabietic, and 27% neutral resinous compounds. The concentration of the constituents of a natural resin can be varied from their relative concentrations as found in nature to yield a derivative that is still a "natural resin" within the meaning of this term, as used herein. Additionally, one or more constituents of a naturally occurring chemical composition such as a rosin, sap, oil, balsam or gum can be isolated or purified to yield a derivative that is a "natural resin" within the meaning of this term. Distillates of natural resins as found in natural sources such as trees, shrubs, plants or seeds are one example of such derivatives. Derivatives formed by any technique, such as isolation or purification methods, to alter the concentration of the constituents or to separate a constituent from other constituents may be used. Additionally, synthetically prepared resin compositions resembling or corresponding to those which occur naturally are within the meaning of the term "natural resin", as used herein.

The term "natural resins" also includes chemical derivatives of naturally occurring chemical compositions obtained from natural sources such as trees, shrubs, plants or seeds. Examples of chemical derivatives include, but are not limited to, maleic modified tall oil, phenolic modified rosin ester resin, maleic modified rosin ester resin, hydrogenated rosin, hydrogenated Canadian balsam, Canadian balsam maleic esters, disproportionated tall oil rosin, and dimerized Tall oil.

If included at all, natural resins are preferably included in a range from about 0.01% to about 50% by weight of the dental bonding composition, more preferably in an amount in a range from about 0.1% to about 35% by weight, and most preferably in a range from about 0.5% to about 20% by weight of the dental bonding composition.

D. Solvents.

It may be desirable to include one or more solvents within dental bonding compositions according to the invention. Solvents may be used to impart a desirable viscosity to the dental bonding composition. Lowering the viscosity may increase the ability of the bonding composition to flow into the dentinal tubules and the undercuts formed by etching the dental substrate. It, thus, may improve the ability of the denting bonding composition to make more intimate contact with, and impregnate into, the conditioned dentin surface. In addition, volatile solvents can quickly evaporate when a layer of the bonding composition is placed onto a dental substrate in order to provide additional adhesion due to increased viscosity and tackiness.

Examples of useful solvents include, but are not limited to, hydrophilic hydrocarbons, hydrophobic hydrocarbons, and water. Hydrophilic solvents are particularly useful since normal dentin is naturally moist. Examples of suitable hydrophilic solvents include ethanol and acetone.

E. Fillers.

Fillers may also be incorporated into the dental bonding composition according to the invention in order to affect the viscosity of the uncured or partially cured composition and/or in order to provide increased strength and hardness of the final cured bonding composition. Fillers may be inert or they may reactive or release active agents.

Examples of particulate fillers used to primarily add strength and hardness are glass particulates. Examples include silica glass and barium oxide glass, which may be added to increase the hardness and durability of the final cured bonding composition. In addition, it may impart desired rheological properties in the uncured and partially cured composition. Because barium oxide glasses can release metals into the bonding compositions that can affect the stability of the polymerizable materials and/or chemical initiators contained therein, it may be desirable to treat barium oxide glass with a protective coating or shell in order to inhibit or prevent unwanted reactions.

When it is desired to use barium oxide glass as a filler within a dental bonding composition according to the invention, it may be advantageous to silanate the barium oxide glass. Silanation is a common procedure used in the art of preparing particulate dental filler materials for use in composite resins, and one of ordinary skill in the art will be readily able to select an appropriate silanating agent that will yield a desired silanated barium oxide glass particulate filler for a given application. Examples of silanating agents include, but are not limited to, 3-methacryloyloxypropyltrimethyl silane, 3-methacryloxypropyltrimethyl silane, 2-ethoxytrimethoxy silane, trimethoxymethyl silane, and trimethoxyvinyl silane.

An example of a particulate filler that is able to release an active agent is calcium fluorosilicate, also referred to as "fluorspar". Fluorspar is a relatively stable mineral substance that, when finely ground and used as a particulate filler, is able to release small, but significant, amounts of fluoride ion into surrounding dental tissues. Fluoride is a well-known mineralizing agent used to strengthen teeth. Hence, the use of fluoride releasing agents such as fluorspar within the dental bonding compositions of the invention can further strengthen and harden the dental tissue surrounding the dental preparation, as well as help to prevent decay.

F. Other Components.

Polymerization inhibitors are often added to polymerization promoters and polymerizable resins at the time of manufacture to inhibit or prevent premature polymerization. If so, the raw polymerizable materials used in manufacturing dental bonding composition according to the invention may include one or more polymerization inhibitors. An example of a polymerization inhibitor is hydroquinone. Of course, it is also within the scope of the invention to deliberately add a polymerization inhibitor to a dental bonding composition according to the invention in order to prevent premature polymerization and curing of the bonding composition.

The dental bonding composition may optionally include additives such as odorants. An example of an odorant is oil of bitter almond.

III. Amalgam Restoratives.

The dental bonding compositions according to the invention are particularly suitable for use with amalgam restorative materials, although the compositions may be adapted for use with other restoratives such as other metal restoratives, composites, and the like. Examples of commonly-used amalgam restorative materials include TYTIN, which is manufactured and sold by Kerr Corporation, located in Orange, Calif., and VALIANT, PH.D., which is distributed in the United States by Vivadent/Ivoclar North America, located in Amherst, N.Y. Amalgams typically include a solid, particulate alloy portion and a liquid mercury portion that, when mixed together (i.e., "triturated"), form a pliable and packable material that cures over time into a hardened filling material.

TYTIN is presently the most commonly-used amalgam restorative in the United States and is available in both normal cure and fast cure embodiments. The alloy within normal curing TYTIN is "spherical" and reportedly includes 59.4% silver, 27.8% tin, and 13.0% copper. The mercury-to-alloy ratio is 42.5%. The alloy within fast curing TYTIN, called TYTIN FC, is reportedly a "modified spherical", high-copper alloy that consists of 61% silver, 26% tin, and 13% copper. The mercury-to-alloy ratio is approximately 43%. The initials "FC" stand for "firm condensation". TYTIN FC is available in two versions: an amalgam that has a carving time of 8–10 minutes and an amalgam that has a carving time of 6–7 minutes.

VALIANT, PH.D. is a palladium-enriched amalgam in which the alloy includes 52.5% silver, 29.7% tin, 17.5% copper, and 0.3% palladium. The alloy portion of the amalgam contains 60% "spherical" particles that comprise 49.5% silver, 30.0% tin, 20.0% copper and 0.5% palladium, and 40% "lathe-cut" particles that comprise 57.0% silver, 29.2% tin and 13.8% copper. The mercury-to-alloy ratio is 42.7%.

TYTIN regular cure amalgam has a compressive strength of 220 MPa after one hour, a compressive strength of 486 MPa after one day, a final tensile strength of 63 MPa, a final creep of 0.07%, and a setting dimensional change ($\mu$n/cm) of −7. VALIANT, PH.D. has a compressive strength after one hour of 210 MPa, a compressive strength after one day of 477 MPa, a tensile strength of 23 MPa measured after one day, a creep of 0.12% measured after 24 hours, and a setting dimensional change of −6.

Presently, TYTIN amalgams comprises a significant majority of the amalgam market share. On the other hand, bond strengths obtained using the inventive compositions and methods disclosed herein have been found to be consistently higher when using VALIANT, PH.D. amalgam rather than TYTIN amalgam.

In general, amalgam restoratives include a solid alloy that is blended with liquid mercury to form an uncured packable material that hardens over time into a very hard and durable restorative material. Amalgam restoratives have been used for more than 150 years, and there have been no known adverse affects resulting from patients being exposed to mercury from their amalgam fillings.

The purpose of the silver is to increase strength, expansion and reactivity, and to decrease creep. Tin is added primarily to react with the mercury, but has the adverse affect of increasing corrosion and decreasing strength and hardness. Copper is added to increase strength, expansion, and hardness and to decrease creep. Zinc may be added in some cases to increase plasticity and strength, while decreasing creep. The mercury is added to wet the alloy particles and to form a pliable, packable material until the metals have been blended to become compounded or bonded. In a compounded or bonded state, mercury does not leach into the patient's body. Nevertheless, although it is not generally publicized, the mercury within the uncured amalgam is a powerful disinfectant that is able to kill much, if not all, of any bacteria within the dental preparation as it comes into contact with the amalgam. It is perhaps for this reason that amalgam fillings often result in lower short-term sensitivity compared to composite restorations.

IV. Methods for Bonding Amalgam Restoratives to a Dental Substrate.

A. Preparatory Steps.

In general, dental substrates to be repaired using amalgam and other restoratives may be prepared in much the same way as dental substrates that are prepared for use with a composite restorative, or substrates for use with an amalgam restorative prepared using conventional methods. It is believed, however, that the bonding compositions and methods according to the invention allow for the removal of less dental tissue when forming an appropriate dental preparation to be filled by the amalgam restorative.

The dental preparations can be formed using any appropriate cutting, grinding or abrading tool known in the art. Once an appropriately sized dental preparation or hollow has been formed in the tooth, it may be further prepared according to methods commonly practiced when using composite restoratives. Whereas conventional amalgam procedures do not require the removal of the smear layer, primarily because no attempt is made to actually bond the amalgam to the tooth, it may be advantageous to treat the tooth to remove the smear layer and to expose the dentin or dentinal tubules in order to improve the bond strength between the bonding composition and the dental substrate.

Dentin contains an enormous number of tubules that radiate outwardly from the pulp chamber. These dentinal tubules are filled with a fluid that is contiguous with the pulp chamber. Although the drilling and cutting of enamel is relatively painless, fluid movement through the dentinal tubules can induce great pain. In addition, once the dentin has been cut, internal pressure within the pulp chamber can cause the fluid within the dentinal tubules to flow out of the tubules and onto the dentinal surface. The cutting of dentin by means of a high speed drill, burr or other cutting or abrading devices, as are typically employed by dentists to clear away tooth decay and shape the dental preparation, can cause the formation of a weakened, semi-attached "smear layer" that remains over the dentin. In addition, the mucous-like fluid from the pulp chamber, which can ooze through the dentin tubules and deposit itself on the smear layer, is not easily dried.

As a result, the smear layer has been a major obstacle to obtaining strong bonds between resinous materials and dentin. Therefore, it is advantageous to remove and/or alter the smear layer. It is then advantageous to seal the dentin tubules to provide a bonding substrate and to prevent fluid movement in the dentin tubules, thereby alleviating or reducing sensitivity. The dental bonding compositions, in addition to enhancing the bond between amalgam and a dental substrate, are advantageously able to seal the dentin and the dentin tubules when using the preferred methods described herein.

A preferred conditioning method entails first contacting the dentin surface with an aqueous acid solution for about 20 seconds in order to remove substantially all of the smear layer, but without damaging the dentin itself. It has been found that aqueous phosphoric acid works well in conditioning the dentin. Nevertheless, any conventional conditioner can be used within the scope of the invention to condition the dentin, including acidic solutions such as aqueous citric acid, nitric acid, and other acids, as well as other known dentin conditioners such as chelators.

Suitable phosphoric acid solutions will typically have a concentration within the range from between about 10% to about 40% (weight to volume), with a concentration of about 35% being preferred. A phosphoric acid solution having a concentration of 35% (weight to volume) is available from Ultradent Products, Inc. located in South Jordan, Utah, under the trademark ULTRAETCH®.

After the smear layer has been substantially removed by the acid solution, excess acid and dissolved and detached materials may be advantageously removed by rinsing the etched surface with water. The rinsed surface may then be dried by means of blowing air, suction or the use of absorbent materials.

If the dental preparation extends completely through the dentin so as to expose the pulp, care should be taken to protect the pulp from strongly acidic compositions or other harsh chemicals to avoid seriously damaging or killing the tooth. Accordingly, before treating the tooth with a conditioner the pulp may be covered by an appropriate pulp capping composition, examples of which include polymerizable and non-polymerizable materials, with or without an antimicrobial agent. Once the pulp has been adequately protected, the dentin can be conditioned as described herein preparatory to bonding an amalgam restorative.

B. Bonding an Amalgam Restorative to a Prepared Dental Substrate.

Once an appropriate dental preparation or other targeted dental substrate has been prepared and optionally conditioned to remove or modify the smear layer as described above, it is ready to receive the amalgam restorative. In order to better illustrate how an amalgam restorative can be bonded to a dental substrate utilizing the inventive dental bonding methods disclosed herein, reference is now made to the drawings.

FIG. 1 illustrates a tooth 10 that has been drilled, cut or otherwise modified so as to include a dental preparation 12 to which an appropriate restorative material is to be placed. It should be understood that FIG. 1 is merely illustrative of a dental preparation and is in no way limiting as to the shape or size of an actual dental preparation that may be appropriate when preparing a tooth according to the invention. In many cases, it will be possible for the dental preparation to be significantly smaller than conventional dental preparations used in conventional amalgam restoration procedures, e.g., formed without overhanging dental tissue designed to mechanically retain the amalgam within the dental preparation, as is generally required using convention amalgam restoration methods.

The dental preparation 12 is preferably cleaned and dried as described above so as to provide a conditioned surface to which a polymerizable material can readily adhere. If during formation of the dental preparation 12 the pulp (not shown) is exposed, any appropriate pulp capping material (not shown) known in the art can be used to cover and protect the pulp.

FIG. 2 illustrates a dental preparation 12 into which a uniform layer of a dental bonding composition 14 has been placed. It should be understood, however, that the thickness and uniformity of the bonding composition 14 in FIG. 2 is merely illustrative. The actual thicknesses and uniformity of the bonding composition 14 may vary considerably from what is depicted in FIG. 2 in actual practice when preparing an actual dental preparation for bonding.

The dental bonding composition 14 may be applied utilizing any application means known in the art, including but not limited to, syringes, spatulas, brushes, picks, and the like. Whereas the dental bonding composition 14 is preferably one of the preferred compositions disclosed herein, it should be understood that any dental bonding composition known in the art can be used so long as it can be partially cured to a desired extent prior to packing an uncured amalgam restorative into the dental preparation 12 and then allowed or caused to continue curing after the amalgam has been packed.

In one embodiment, the dental bonding composition may include one or more polymerization photoinitiators that trigger polymerization of the one or more polymerizable materials within the dental bonding composition upon exposing the composition to radiant energy 16 (e.g., from a light curing device 18), as illustrated in FIG. 3. In a preferred embodiment, the amount of photoinitiator is selected to only partially polymerize or cure the composition, as described more fully above, when exposing the composition to an excess of light. In other embodiments, it may be possible to simply irradiate a light-curable bonding composition for a shorter period of time than would be necessary to fully cure the composition, i.e., for a period of time that causes only partial polymerization of the bonding composition. Whether the dental bonding composition is specially formulated to only partially polymerize when exposed to an excess of light, or whether the practitioner deliberately restricts the intensity and/or duration of the radiant energy in order to only partially cure the bonding composition, FIG. 3 illustrates the general use of radiant energy 16 emitted from a dental curing light 18 to partially cure the dental bonding composition 14.

After the dental bonding composition has been partially cured an appropriate amount, the dental preparation 12 is ready to receive the uncured amalgam restoration material. FIG. 4 illustrate a dental bonding composition that is partially cured and that includes two distinct layers that are partially cured to different extents. Although the differential in partial curing may be multi-layered, or be in the form of a gradient rather than distinct layers, FIG. 4 is useful in generally illustrating the effect of this differential in partial curing. As illustrated, the partially cured dental bonding composition 14 comprises an interior layer 20 that is adjacent to the surface 22 of the dental preparation 12 and that is more fully cured than the exposed upper layer 24 of the bonding composition 14.

Without being limited to any particular theory, it is believed that the exposed layer 24 remains in a less cured or polymerized state compared to the interior layer 20 because of the polymerization-retarding effect of air. More particularly, the oxygen within air is believed to inhibit polymerization so that the exposed layer 24 comprises an "inhibition" or "inhibited" layer that is significantly less cured than the interior layer 20 adjacent to the dental preparation surface 22. As a result, the exposed layer 24 is considerably more easily deformed and disrupted than the interior layer 20, which is beneficial as described herein.

FIG. 5 illustrates the act of packing or condensing an uncured amalgam restorative 26 into the dental preparation 12 by means of a conventional amalgam packing tool 28. It should be understood, however, that the uncured amalgam 26 may be packed within the dental preparation 12 using any appropriate tool or packing means. In the alternative, other flowable metal restoratives may be used instead of amalgam. Nevertheless, amalgam restoratives are preferred due to their low cost, ready availability and ease of use.

In general, uncured amalgam restoratives are viscous pastes that are packed into the dental preparations by means of short, but firm, downward thrusts with the packing tool in order to cause the amalgam to spread out and fill the dental preparation. Significant force is generally necessary to pack the amalgam firmly within the dental preparation. One of the advantages of packing an uncured amalgam restorative into a dental preparation using a packing tool is that the combined action of the packing tool and amalgam causes significant disruption of the deformable bonding composition, particularly the less fully cured inhibition layer.

Figure 6:
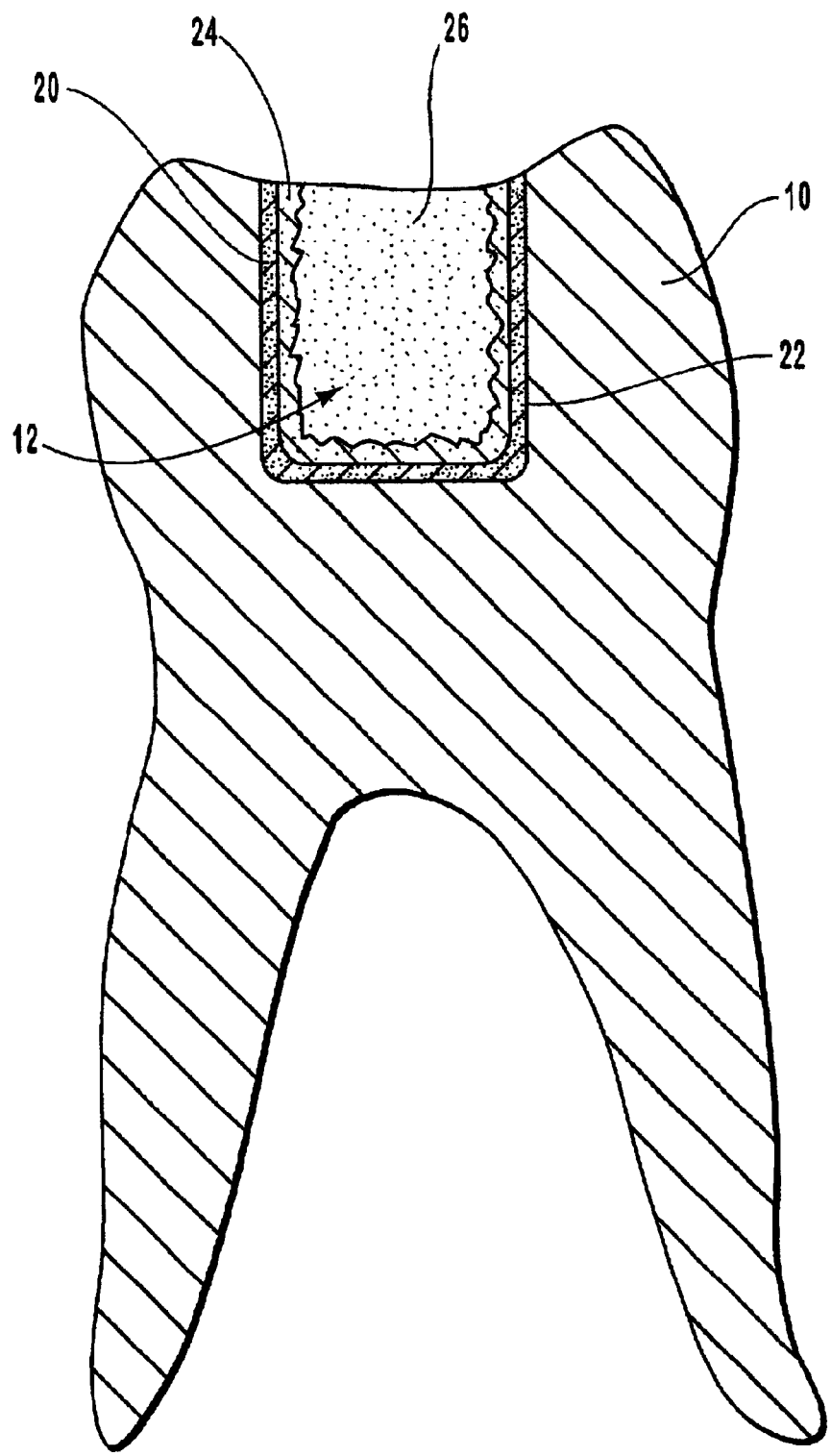
FIG. 6 is a side cross-section view of the tooth of FIG. 5 after the uncured amalgam restorative material has been fully packed into the dental preparation using an appropriate amalgam packing tool.

FIG. 6 generally illustrates the effect of packing an uncured amalgam 26 into a dental preparation 12 in order to physically disrupt the exterior inhibition layer 24 of the partially cured bonding composition. The upper layer 24 is disrupted and moved around so as to form troughs, peaks and other irregularities that increase the mechanical interface between the bonding composition and the amalgam. Fingers of the bonding composition may extend into the amalgam so as to form roots that firmly anchor the bonding composition and amalgam together upon curing. It should be understood that the disrupted layer 24 depicted in FIG. 6 is for illustrative purposes only. The actual shape and degree of disruption may vary greatly from tooth to tooth and in actual dental restoration procedures.

Assuming that the uncured amalgam 26 is packed within the dental preparation 12 in a manner so as to displace all (or substantially all) of the air, the uncured amalgam 26 will assume a conformation that is generally complementary to the conformation of the disrupted inhibition layer 24 of the bonding composition 14. After both the bonding composition 14 and amalgam 26 have become substantially hardened or cured, the irregular, but complementary, interface between the two provide a significant increase in final bond strength of the tooth restoration compared to conventional amalgam restoration methods. The troughs, peaks, fingers, roots, and other irregularities of the dental bonding composition and the corresponding irregularities within the amalgam composition act to mechanically lock the two substances together. It may be useful to think of the interaction as the interaction of complementary puzzle pieces.

The interior layer 20, because it is more fully cured than the exposed layer 24, resists being displaced during packing of the uncured amalgam 26 into the dental preparation 12. Because the interior layer 20 is more fully cured than the exposed layer 24, it forms a more durable bond with the dental preparation surface 22 and it also resists being moved or disrupted during compaction of the amalgam, both of which ensure a more reliable bond between the dental bonding composition 14 and the dental preparation surface 22.

Figure 7:
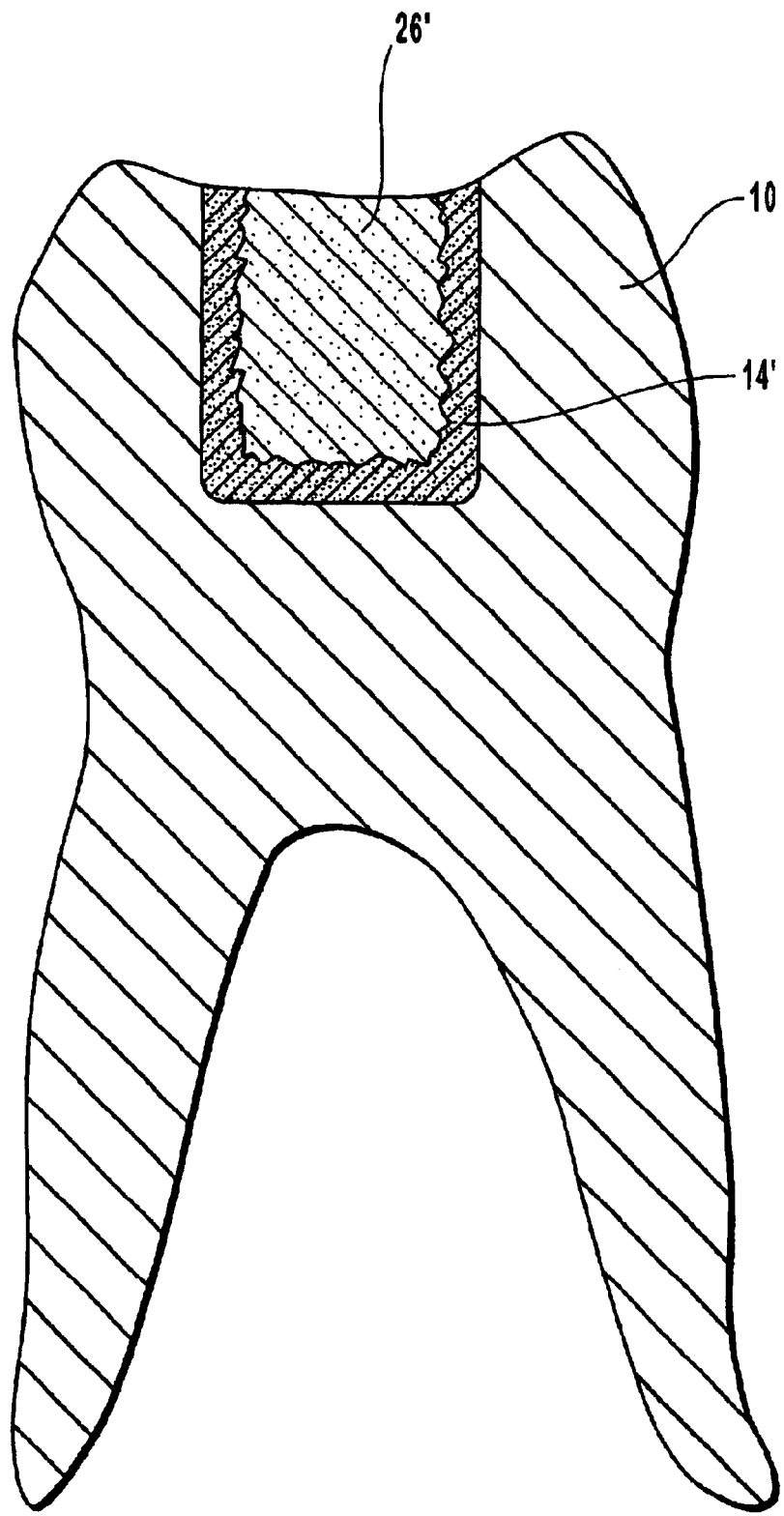
FIG. 7 is a side cross-section view of the tooth of FIG. 6 after the amalgam and dental bond composition have cured.

FIG. 7 illustrates a restored tooth 10 in which the initially partially cured bonding composition 14 has cured or substantially cured into hardened bonding composition 14' and the initially uncured amalgam 26 has cured or substantially cured into hardened amalgam 26'. In a preferred embodiment, the interaction between the uncured amalgam 26 and the partially cured bonding composition 14 triggers the further polymerization or curing of the bonding composition.

For example, chemical initiators such as benzoyl peroxide, though relatively stable when mixed with polymerizable materials, become unstable when contacted with the uncured amalgam. It is believed that one or more metals within the amalgam trigger the decomposition of the benzoyl peroxide and that the decomposition products, in turn, cause the partially cured polymerizable material within the bonding composition to continue curing. Displacement of the air and accompanying oxygen by the amalgam restorative from the dental preparation facilitates further polymerization of the inhibition layer.

Even though FIG. 3 depicts light curing to partially polymerize the dental bonding composition 14, it may be possible in an alternative embodiment to simply include one or more chemical initiators instead of a photoinitiator. A chemical initiator such as benzoyl peroxide (with or without a tertiary amine) may be mixed into the bonding composition in a manner so as to cause controlled polymerization of the bonding composition over a prescribed time period. This allows the bonding composition to be placed within the dental preparation (see FIG. 2) within a first prescribed time period. After a second prescribed time period during which the dental bonding composition has been partially cured to an appropriate extent (see FIG. 4), an uncured amalgam may be introduced into the dental preparation (see FIGS. 5 and 6). Thereafter, the chemical initiator causes the polymerizable material to continue curing after packing the amalgam into the dental preparation (see FIG. 7). The amalgam may cause further acceleration of the polymerization process in some cases for reasons described herein.

The foregoing methods are useful for increasing the bond strength between an amalgam restorative and a dental substrate. Any positive bond between the amalgam and substrate would be an advance in the art of amalgam restorations that do not use a bonding agent. Thus, bond strengths greater than 1 MPa would be an advancement over conventional amalgam restoration techniques. Nevertheless, the compositions and methods disclosed herein preferably yield a bond strength between the amalgam restorative and a dental substrate greater than about 15 MPa, more preferably greater than about 20 MPa, and most preferably greater than about 25 MPa.

V. Examplary Bonding Compositions.

The following examples are provided in order to illustrate various bonding compositions related to the present invention. Examples 1–24 disclose bonding compositions that were actually prepared, all of which were found to improve the bond strength between a dental substrate and amalgam compared to conventional amalgam restoration procedures that do not use a bonding agent. Bond strengths of up to 37 MPa were obtained, although there was considerable variability in the bond strengths obtained when testing the compositions of Examples 1–24. Examples 25–28 describe hypothetical, or prophetic, examples of dental bonding compositions according to the invention. While examples 25–28 are hypothetical in nature, they are based upon actual mix designs that have been tested or contemplated and are presented in this form in order to more completely illustrate the full scope of the invention.

EXAMPLE 1

A dental bonding composition suitable for use in increasing the bond strength between a dental substrate and an amalgam restorative material was formed from the following components:

| Component | Concentration (wt. %) |
| --- | --- |
| Bis Glycerol Methacrylate Phosphate | 19.6 |
| 2-Hydroxyethyl Methacrylate (HEMA) | 21.2 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Tolu Resinoid | 0.7 |
| Phosphine Oxide, phenyl bis(2,4,6-trimethyl benzoyl) | 0.06 |
| 2-Hydroxy-2-methyl-1-phenyl-1-propanone | 0.04 |
| Bis-GMA | 5.0 |
| Benzoyl Peroxide | 0.8 |

EXAMPLE 2

A dental bonding composition suitable for use in increasing the bond strength between a dental substrate and an amalgam restorative material was formed from the following components:

| Component | Concentration (wt. %) |
| --- | --- |
| Bis-Glyceryl Methacrylate Phosphate | 19.6 |
| HEMA | 20.3 |
| Barium Oxide Glass (silanated) | 17.0 |
| Fluorspar | 15.0 |
| Fumed Aluminum Oxide | 8.0 |
| Ethanol | 4.25 |
| Acetone | 4.25 |
| Methacrylic Acid | 4.1 |
| Tolu Resinoid | 0.7 |
| Phosphine Oxide, phenyl bis(2,4,6-trimethyl benzoyl) | 0.06 |
| 2-Hydroxy-2-methyl-1-phenyl-1-propanone | 0.04 |
| Bis-GMA | 5.0 |
| Benzoyl Peroxide | 0.8 |

EXAMPLE 3

A dental bonding composition suitable for use in increasing the bond strength between a dental substrate and an amalgam restorative material was formed from the following components:

| Component | Concentration (wt. %) |
| --- | --- |
| Bis Glycerol Methacrylate Phosphate | 19.6 |
| HEMA | 21.95 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Bis-GMA | 5.0 |
| Benzoyl Peroxide | 0.8 |

EXAMPLE 4

A dental bonding composition suitable for use in increasing the bond strength between a dental substrate and an amalgam restorative material was formed from the following components:

| Component | Concentration (wt. %) |
| --- | --- |
| Bis Glycerol Methacrylate Phosphate | 19.6 |
| HEMA | 16.3 |
| Barium Oxide Glass (silanated) | 17.0 |
| Fluorspar | 15.0 |
| Fumed Aluminum Oxide | 7.0 |
| Ethanol | 8.5 |
| Methacrylic Acid | 4.1 |
| Tolu Resinoid | 0.7 |
| Phosphine Oxide, phenyl bis(2,4,6-trimethyl benzoyl) | 0.06 |
| 2-Hydroxy-2-methyl-1-phenyl-1-propanone | 0.04 |
| Bis-GMA | 10.0 |
| Benzoyl Peroxide | 0.8 |

EXAMPLE 5

A dental bonding composition suitable for use in increasing the bond strength between a dental substrate and an amalgam restorative material was formed from the following components:

| Component | Concentration (wt. %) |
| --- | --- |
| Bis Glycerol Methacrylate Phosphate | 19.6 |
| HEMA | 16.3 |
| Barium Oxide Glass (silanated) | 17.0 |
| Fluorspar | 15.0 |

| Component | Concentration (wt. %) |
|---|---|
| Fumed Aluminum Oxide | 8.0 |
| Ethanol | 8.5 |
| Methacrylic Acid | 4.1 |
| Tolu Resinoid | 0.7 |
| Phosphine Oxide, phenyl bis(2,4,6-trimethyl benzoyl) | 0.06 |
| 2-Hydroxy-2-methyl-1-phenyl-1-propanone | 0.04 |
| Bis-GMA | 5.0 |
| Benzoyl Peroxide | 0.8 |

EXAMPLE 6

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 19.6 |
| HEMA | 21.275 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Tolu Resinoid | 0.7 |
| Phosphine Oxide, phenyl bis(2,4,6-trimethyl benzoyl) | 0.015 |
| 2-Hydroxy-2-methyl-1-phenyl-1-propanone | 0.01 |
| Bis-GMA | 5.0 |
| Benzoyl Peroxide | 0.8 |

EXAMPLE 7

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 19.6 |
| HEMA | 26.275 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Tolu Resinoid | 0.7 |
| Phosphine Oxide, phenyl bis(2,4,6-trimethyl benzoyl) | 0.015 |
| 2-Hydroxy-2-methyl-1-phenyl-1-propanone | 0.01 |
| Benzoyl Peroxide | 0.8 |

EXAMPLE 8

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 19.6 |
| HEMA | 21.1 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Tolu Resinoid | 0.7 |
| Phosphine Oxide, phenyl bis(2,4,6-trimethyl benzoyl) | 1.0 |
| Bis-GMA | 5.0 |

EXAMPLE 9

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 19.6 |
| HEMA | 14.1 |
| Barium Oxide Glass (silanated) | 17.0 |
| Fluorspar | 15.0 |
| Fumed Aluminum Oxide | 5.0 |
| Ethanol | 8.5 |
| Methacrylic Acid | 4.1 |
| Tolu Resinoid | 0.7 |
| Phosphine Oxide, phenyl bis(2,4,6-trimethyl benzoyl) | 0.06 |
| 2-Hydroxy-2-methyl-1-phenyl-1-propanone | 0.04 |
| Bis-GMA | 5.0 |

EXAMPLE 10

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 19.6 |
| HEMA | 17.1 |
| Barium Oxide Glass (silanated) | 17.0 |
| Fluorspar | 15.0 |
| Fumed Aluminum Oxide | 7.0 |
| Ethanol | 8.5 |
| Methacrylic Acid | 4.1 |
| Tolu Resinoid | 0.7 |
| Phosphine Oxide, phenyl bis(2,4,6-trimethyl benzoyl) | 0.06 |
| 2-Hydroxy-2-methyl-1-phenyl-1-propanone | 0.04 |
| Bis-GMA | 10.0 |

EXAMPLE 11

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 19.6 |
| HEMA | 21.95 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Bis-GMA | 5.0 |
| Benzoyl Peroxide | 0.8 |

EXAMPLE 12

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 19.6 |
| HEMA | 17.8 |
| Barium Oxide Glass (silanated) | 17.0 |
| Fluorspar | 15.0 |
| Fumed Aluminum Oxide | 7.0 |
| Ethanol | 8.5 |
| Methacrylic Acid | 4.1 |
| Tolu Resinoid | 0.7 |
| Phosphine Oxide, phenyl bis(2,4,6-trimethyl benzoyl) | 0.06 |
| 2-Hydroxy-2-methyl-1-phenyl-1-propanone | 0.04 |
| Bis-GMA | 10.0 |

EXAMPLE 13

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 19.4 |
| HEMA | 17.7 |
| Barium Oxide Glass (silanated) | 16.9 |
| Fluorspar | 14.9 |
| Fumed Aluminum Oxide | 6.9 |
| Ethanol | 8.4 |
| Methacrylic Acid | 4.1 |
| Tolu Resinoid | 0.7 |
| Phosphine Oxide, phenyl bis(2,4,6-trimethyl benzoyl) | 0.06 |
| 2-Hydroxy-2-methyl-1-phenyl-1-propanone | 0.04 |
| Bis-GMA | 9.9 |
| Benzoyl Peroxide | 0.8 |

EXAMPLE 14

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 32.7 |
| HEMA | 33.8 |
| Ethanol | 14.2 |
| Methacrylic Acid | 6.8 |
| Tolu Resinoid | 1.2 |
| Phosphine Oxide, phenyl bis(2,4,6-trimethyl benzoyl) | 1.0 |
| 2-Hydroxy-2-methyl-1-phenyl-1-propanone | 0.7 |
| Bis-GMA | 8.3 |
| Benzoyl Peroxide | 1.3 |

EXAMPLE 15

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 32.1 |
| HEMA | 22.0 |
| Barium Oxide Glass (silanated) | 17.0 |
| Fluorspar | 15.0 |
| Fumed Aluminum Oxide | 9.0 |
| Methacrylic Acid | 4.1 |
| Tolu Resinoid | 0.7 |
| Phosphine Oxide, phenyl bis(2,4,6-trimethyl benzoyl) | 0.03 |
| 2-Hydroxy-2-methyl-1-phenyl-1-propanone | 0.02 |
| Benzoyl Peroxide | 0.8 |

EXAMPLE 16

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 28.1 |
| HEMA | 21.95 |
| Barium Oxide Glass (silanated) | 17.0 |
| Fluorspar | 15.0 |
| Fumed Aluminum Oxide | 8.0 |
| Methacrylic Acid | 4.1 |
| Tolu Resinoid | 0.7 |
| Phosphine Oxide, phenyl bis(2,4,6-trimethyl benzoyl) | 0.03 |
| 2-Hydroxy-2-methyl-1-phenyl-1-propanone | 0.02 |
| Bis-GMA | 5.0 |
| Benzoyl Peroxide | 0.8 |

EXAMPLE 17

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 21.1 |
| HEMA | 21.95 |
| Barium Oxide Glass (silanated) | 17.0 |
| Fluorspar | 15.0 |
| Fumed Aluminum Oxide | 10.0 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Bis-GMA | 5.0 |
| Benzoyl Peroxide | 0.8 |
| Calcium Hydroxyapatite | 5.0 |

EXAMPLE 18

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 28.9 |
| HEMA | 21.95 |
| Barium Oxide Glass (silanated) | 17.0 |
| Fluorspar | 15.0 |
| Fumed Aluminum Oxide | 8.0 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Bis-GMA | 5.0 |

EXAMPLE 19

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 25.1 |
| HEMA | 21.95 |
| Barium Oxide Glass (silanated) | 16.0 |
| Fluorspar | 15.0 |
| Fumed Aluminum Oxide | 9.0 |
| Ethanol | 8.0 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Benzoyl Peroxide | 0.8 |

EXAMPLE 20

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 20.5 |
| HEMA | 35.0 |
| Barium Oxide Glass (silanated) | 16.0 |
| Fluorspar | 15.0 |
| Fumed Aluminum Oxide | 9.0 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Benzoyl Peroxide | 0.8 |

EXAMPLE 21

A dental bonding composition suitable for use in increasing the bond strength between a dental substrate and an amalgam restorative material was formed from the following components:

| Component | Concentration (wt %) |
|---|---|
| Bis Glycerol Methacrylate Phosphate | 21.1 |
| HEMA | 21.95 |
| Barium Oxide Glass (silanated) | 15.0 |
| Fluorspar | 15.0 |
| Fumed Aluminum Oxide | 10.0 |
| Ethanol | 12.0 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Benzoyl Peroxide | 0.8 |

EXAMPLE 22

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 24.43 |
| HEMA | 21.95 |
| Barium Oxide Glass (silanated) | 17.0 |
| Fluorspar | 15.0 |
| Fumed Aluminum Oxide | 8.0 |
| Ethanol | 8.0 |
| Methacrylic Acid | 4.1 |
| Phosphine Oxide, phenyl bis(2,4,6-trimethyl benzoyl) | 0.02 |
| Benzoyl Peroxide | 1.5 |

EXAMPLE 23

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 21.0 |
| HEMA | 20.05 |
| Barium Oxide Glass (silanated) | 11.0 |
| Fluorspar | 15.0 |
| Fumed Aluminum Oxide | 14.0 |
| Ethanol | 16.0 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Benzoyl Peroxide | 0.8 |

EXAMPLE 24

A dental bonding composition suitable for use in increasing the bond strength between a dental substrate and an amalgam restorative material was formed from the following components:

| Component | Concentration (wt. %) |
|---|---|
| Bis Glycerol Methacrylate Phosphate | 19.6 |
| HEMA | 21.95 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Bis-GMA | 5.0 |
| Benzoyl Peroxide | 0.8 |

EXAMPLE 25

A dental bonding composition suitable for use in increasing the bond strength between a dental substrate and an amalgam restorative material is formed from the following components:

| Component | Concentration (wt. %) |
|---|---|
| Bis Glycerol Methacrylate Phosphate | 20.1 |
| HEMA | 22.45 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Bis-GMA | 4.0 |
| Benzoyl Peroxide | 0.8 |

The bonding composition of Example 25 is similar to the composition of Example 24, except that the concentration of Bis-GMA is reduced to 4.0%, and the concentrations of bis glycerol methacrylate phosphate and HEMA are each increased by 0.5%. Based on an extrapolation of actual test results, the bond strength obtained when using the composition of Example 25 to bond an amalgam to a dental substrate exceeds, or would be expected to exceed, the bond strength obtained when using the composition of Example 24 to bond an amalgam to a dental substrate.

EXAMPLE 26

A dental bonding composition suitable for use in increasing the bond strength between a dental substrate and an amalgam restorative material is formed from the following components:

| Component | Concentration (wt. %) |
|---|---|
| Bis Glycerol Methacrylate Phosphate | 20.6 |
| HEMA | 22.95 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Bis-GMA | 3.0 |
| Benzoyl Peroxide | 0.8 |

The bonding composition of Example 26 is similar to the composition of Example 24, except that the concentration of Bis-GMA is reduced to 3.0%, and the concentrations of bis glycerol methacrylate phosphate and HEMA are each increased by 1.0%. Based on an extrapolation of actual test results, the bond strength obtained when using the composition of Example 26 to bond an amalgam to a dental substrate exceeds, or would be expected to exceed, the bond strengths obtained when using the compositions of Examples 24 and 25 to bond an amalgam to a dental substrate.

EXAMPLE 27

A dental bonding composition suitable for use in increasing the bond strength between a dental substrate and an amalgam restorative material is formed from the following components:

| Component | Concentration (wt. %) |
|---|---|
| Bis Glycerol Methacrylate Phosphate | 21.1 |
| HEMA | 23.45 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Bis-GMA | 2.0 |
| Benzoyl Peroxide | 0.8 |

The bonding composition of Example 27 is similar to the composition of Example 24, except that the concentration of Bis-GMA is reduced to 2.0%, and the concentrations of bis glycerol methacrylate phosphate and HEMA are each increased by 1.5%. Based on an extrapolation of actual test results, the bond strength obtained when using the composition of Example 27 to bond an amalgam to a dental substrate exceeds, or would be expected to exceed, the bond strengths obtained when using the compositions of Examples 24–26 to bond an amalgam to a dental substrate.

EXAMPLE 28

A dental bonding composition suitable for use in increasing the bond strength between a dental substrate and an amalgam restorative material is formed from the following components:

| Component | Concentration (wt. %) |
| --- | --- |
| Bis Glycerol Methacrylate Phosphate | 21.6 |
| HEMA | 23.95 |
| Barium Oxide Glass (silanated) | 17.0 |
| Fluorspar | 15.0 |
| Fumed Aluminum Oxide | 8.0 |
| Ethanol | 8.5 |
| Methacrylic Acid | 4.1 |
| Phosphine Oxide, phenyl bis(2,4,6-trimethyl benzoyl) | 0.03 |
| 2-Hydroxy-2-methyl-1-phenyl-1-propanone | 0.02 |
| Bis-GMA | 1.0 |
| Benzoyl Peroxide | 0.8 |

The bonding composition of Example 28 is similar to the composition of Example 24, except that the concentration of Bis-GMA is reduced to 1.0%, and the concentrations of bis glycerol methacrylate phosphate and HEMA are each increased by 2.0%. Based on an extrapolation of actual test results, the bond strength obtained when using the composition of Example 28 to bond an amalgam to a dental substrate exceeds, or would be expected to exceed, the bond strengths obtained when using the compositions of Examples 24–27 to bond an amalgam to a dental substrate.

VI. Summary.

The present invention provides compositions and methods for bonding an amalgam restorative to a dental substrate. Preferred compositions according to the invention are able to cure in steps so that the amalgam restorative can be packed against a partially cured dental bonding composition that remains deformable and so that the bonding composition continues to cures or harden after placement of the amalgam restorative within the dental preparation. Preferred methods cure any suitable bonding composition in steps so as to provide increased bond strengths as described herein. The compositions and methods provide for increased bond strength between the amalgam restorative and the dental substrate. In a preferred method of use, the preferred compositions and methods may allow the dental practitioner to remove less of the tooth than would otherwise be required using standard amalgam restoration procedures.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dental composition for bonding an amalgam restorative to a dental substrate, comprising:

at least one polymerizable material;

at least one photoinitiator in an amount so that a portion of the dental composition at least partially polymerizes and adheres to a dental substrate when the dental composition is exposed to radiant energy and at least a portion of an exposed surface of the polymerizable material remains at least partially unpolymerized and deformable when the dental composition is exposed to radiant energy to initiate polymerization of the polymerizable material during use; and at least one chemical initiator that does not cause the polymerizable material to polymerize when initially mixed therewith but that causes further polymerization of the polymerizable material when the dental composition is contacted with an amalgam restorative during use.

2. A dental composition as defined in claim 1, wherein the polymerizable material comprises at least one polymerizable promoter.

3. A dental composition as defined in claim 2, wherein the polymerizable promotor comprises at least one of a monomer, oligomer or other prepolymer having at least one ethylenically unsaturated group and at least one carboxylic acid group.

4. A dental composition as defined in claim 2, wherein the polymerizable promotor comprises, or is an oligomer of, at least one monomer having the formula:

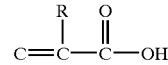

wherein R is a hydrogen radical, a methyl group, a saturated aliphatic radical, an unsaturated aliphatic radical, a halogen radical or a CN radical.

5. A dental composition as defined in claim 2, wherein the polymerizable promotor comprises at least one of methacrylic acid or acrylic acid.

6. A dental composition as defined in claim 2, wherein the polymerizable promotor comprises, or is an oligomer of, at least one monomer having the formula:

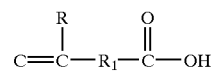

wherein R is a hydrogen radical, a methyl group, a saturated aliphatic radical, an unsaturated aliphatic radical, a halogen radical or a CN radical; and wherein $R_1$ is at least one oxygen radical, a saturated aliphatic radical, a saturated aliphatic radical interrupted by at least one oxygen or other polar radical, an unsaturated aliphatic radical, an unsaturated aliphatic radical interrupted by at least one oxygen or other polar radical, a homocyclic radical, a heterocyclic radical, a polymerizable moiety, or an aryl radical having four to six carbon atoms and a valency of n+1, with n being an integer of at least 6.

7. A dental composition as defined in claim 6, wherein the polymerizable promoter comprises at least one of 4-pentenoic acid, 6-heptenoic acid, or 2,2-dimethyl-4-pentenoic acid.

8. A dental composition as defined in claim 2, wherein the polymerizable promotor has a concentration in a range of about 0.5% to about 60% by weight of the dental composition.

9. A dental composition as defined in claim 2, wherein the polymerizable promotor has a concentration in a range of about 0.75% to about 50% by weight of the dental composition.

10. A dental composition as defined in claim 2, wherein the polymerizable promotor has a concentration in a range of about 1% to about 40% by weight of the dental composition.

11. A dental composition as defined in claim 1, wherein the polymerizable material comprises at least one polymerizable resin.

12. A dental composition as defined in claim 11, wherein the polymerizable resin comprises at least one of a hydrophilic resin having at least one hydroxy group or a hydrophobic resin.

13. A dental composition as defined in claim 11, wherein the polymerizable resin comprises at least one of hydroxyalkyl methacrylate, hydroxyalkyl acrylate, alkyl methacrylate or alkyl acrylate.

14. A dental composition as defined in claim 11, wherein the polymerizable resin comprises at least one of HEMA, Bis-GMA, glycerol dimethacrylate, methyl acrylate, methyl methacrylate, or triethylene glycol dimethacrylate.

15. A dental composition as defined in claim 14, wherein the Bis-GMA has a concentration of less than about 4% by weight of the dental composition.

16. A dental composition as defined in claim 14, wherein the Bis-GMA has a concentration of less than about 3% by weight of the dental composition.

17. A dental composition as defined in claim 14, wherein the Bis-GMA has a concentration of less than about 2% by weight of the dental composition.

18. A dental composition as defined in claim 11, wherein the polymerizable resin comprises at least one of the following groups:

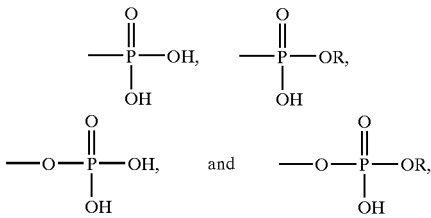

wherein R is an alkyl.

19. A dental composition as defined in claim 11, wherein the polymerizable resin comprises at least one of bis glycerol methacrylate phosphate, bis 2-hydroxy ethyl methacrylate phosphate, phosphate ester of p-hydroxyphenyl methacrylamide, phosphate ester of 3-hydroxy propyl methacrylate, or phosphate ester of 4-hydroxy butyl methacrylate.

20. A dental composition as defined in claim 11, wherein the polymerizable resin has a concentration in a range of about 0.5% to about 60% by weight of the dental composition.

21. A dental composition as defined in claim 11, wherein the polymerizable resin has a concentration in a range of about 0.75% to about 50% by weight of the dental composition.

22. A dental composition as defined in claim 11, wherein the polymerizable resin has a concentration in a range of about 1% to about 40% by weight of the dental composition.

23. A dental composition as defined in claim 1, wherein the photoinitiator comprises at least one α-diketone.

24. A dental composition as defined in claim 1, wherein the photoinitiator comprises at least one of camphoroquinone, benzoin methyl ether, benzophenone or 9,10-anthraquinone.

25. A dental composition as defined in claim 1, wherein the photoinitiator comprises at least one of phenyl bis(2,4, 6-trimethyl benzoyl) phosphine oxide or 2-hydroxy-2-methyl-1-phenyl-1-propanone.

26. A dental composition as defined in claim 1, wherein the photoinitiator has a concentration less than an amount that is stoichiometrically required to cause complete polymerization of the polymerizable material if irradiated with an excess of radiant energy.

27. A dental composition as defined in claim 1, wherein the photoinitiator has a concentration in a range of about 0.001% to about 0.5% by weight of the dental composition.

28. A dental composition as defined in claim 1, wherein the photoinitiator has a concentration in a range of about 0.005% to about 0.2% by weight of the dental composition.

29. A dental composition as defined in claim 1, wherein the photoinitiator has a concentration in a range of about 0.008% to about 0.08% by weight of the dental composition.

30. A dental composition as defined in claim 1, wherein the chemical initiator comprises at least one peroxide.

31. A dental composition as defined in claim 30, wherein the chemical initiator comprises benzoyl peroxide.

32. A dental composition as defined in claim 30, wherein the chemical initiator comprises at least one of 2-butanone peroxide, lauroyl peroxide or tert-butyl peroxide.

33. A dental composition as defined in claim 1, wherein the chemical initiator has a concentration in a range of about 0.001% to about 5% by weight of the dental composition.

34. A dental composition as defined in claim 1, wherein the chemical initiator has a concentration in a range of about 0.01% to about 3% by weight of the dental composition.

35. A dental composition as defined in claim 1, wherein the chemical initiator has a concentration in a range from about 0.1% to about 2% of the dental composition.

36. A dental composition as defined in claim 1, further including at least one natural resin.

37. A dental composition as defined in claim 36, wherein the natural resin comprises at least one of a rosin, distillate, sap, oil, balsam, gum, an isolated constituent of one of the foregoing, a modification of one of the foregoing, or a synthetic replication of one of the foregoing.

38. A dental composition as defined in claim 36, wherein the natural resin comprises at least one of Canadian balsam, sandarac, mastic, pontianak, copal, manilla, peruvian, benzoin, elemi, opopanax, olibanum, styrax, benzoin siam, tolu, resinoid, tall, pine, or eugenol.

39. A dental composition as defined in claim 1, further including at least one particulate filler.

40. A dental composition as defined in claim 39, wherein the particulate filler comprises at least one glass.

41. A dental composition as defined in claim 40, wherein the glass comprises barium oxide glass.

42. A dental composition as defined in claim 41, wherein at least a portion of the barium oxide glass has been silanated.

43. A dental composition as defined in claim 39, wherein the particulate filler comprises at least one fluoride-releasing compound.

44. A dental composition as defined in claim 43, wherein the fluoride-releasing compound comprises at least one calcium fluorosilicate.

45. A dental composition as defined in claim 1, further including at least one solvent.

46. A dental composition as defined in claim 45, wherein the solvent comprises at least one of a hydrophilic hydrocarbon, hydrophobic hydrocarbon, or water.

47. A dental composition as defined in claim 45, wherein the solvent comprises at least one of ethanol or acetone.

48. A dental composition as defined in claim 1, further including at least one polymerization inhibitor.

49. A dental composition as defined in claim 1, wherein the dental composition, when used to bond an amalgam restorative to a dental substrate, yields a final bond strength between the amalgam restorative and dental substrate of at least about 15 MPa.

50. A dental composition as defined in claim 1, wherein the dental composition, when used to bond an amalgam restorative to a dental substrate, yields a final bond strength between the amalgam restorative and dental substrate of at least about 20 MPa.

51. A dental composition as defined in claim 1, wherein the dental composition, when used to bond an amalgam restorative to a dental substrate, yields a final bond strength between the amalgam restorative and dental substrate of at least about 25 MPa.

52. A dental composition as defined in claim 1, wherein the dental composition is a stable, one-part composition.

53. A dental composition as defined in claim 1, wherein the dental composition initially comprises multiple parts that are mixed together shortly before application to a dental substrate.

54. A dental composition as defined in claim 1, wherein the chemical initiator is initially stable when mixed with the photoinitiator and polymerizable material but decomposes when exposed to one or more metals contained in an amalgam restorative.

55. A dental composition for bonding an amalgam restorative to a dental substrate, comprising:
at least one polymerizable material;
at least one photoinitiator in an amount that is less than what is stoichiometrically required to cause complete polymerization of the polymerizable material if irradiated with radiant energy in the absence of oxygen; and
at least one chemical initiator that is initially stable when mixed with the photoinitiator and polymerizable material but that decomposes when exposed to one or more metals contained in an amalgam restorative in order to cause further polymerization of the polymerizable material when the dental composition comes into contact with the amalgam restorative.

56. A dental composition as defined in claim 55, wherein the polymerizable material comprises at least one polymerizable promotor that comprises at least one of a monomer, oligomer or other prepolymer having at least one ethylenically unsaturated group and at least one carboxylic acid group.

57. A dental composition as defined in claim 56, wherein the polymerizable promotor comprises, or is an oligomer of, at least one monomer having the formula:

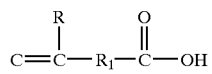

wherein R is a hydrogen radical, a methyl group, a saturated aliphatic radical, an unsaturated aliphatic radical, a halogen radical or a CN radical; and wherein $R_1$ is a chemical bond, at least one an oxygen radical, a saturated aliphatic radical, a saturated aliphatic radical interrupted by at least one oxygen or other polar radical, an unsaturated aliphatic radical, an unsaturated aliphatic radical interrupted by at least one oxygen or other polar radical, a homocyclic radical, a heterocyclic radical, a polymerizable moiety, or an aryl radical having four to six carbon atoms and a valency of n+1, with n being an integer of at least 6.

58. A dental composition as defined in claim 56, wherein the polymerizable promotor comprises at least one of methacrylic acid, acrylic acid, 4-pentenoic acid, 6-heptenoic acid, or 2,2-dimethyl-4-pentenoic acid.

59. A dental composition as defined in claim 55, wherein the polymerizable material comprises at least one polymerizable resin that comprises at least one of a hydrophilic resin having at least one hydroxy group or a hydrophobic resin.

60. A dental composition as defined in claim 59, wherein the polymerizable resin comprises at least one of hydroxyalkyl methacrylate, hydroxyalkyl acrylate, alkyl methacrylate, alkyl acrylate, HEMA, Bis-GMA, glycerol dimethacrylate, methyl acrylate, methyl methacrylate, or triethylene glycol dimethacrylate.

61. A dental composition as defined in claim 60, wherein the Bis-GMA has a concentration of less than about 4% by weight of the dental composition.

62. A dental composition as defined in claim 59, wherein the polymerizable resin comprises at least one of the following groups:

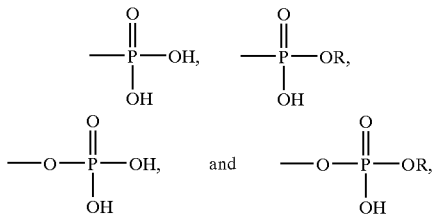

wherein R is an alkyl.

63. A dental composition for bonding an amalgam restorative to a dental substrate, comprising:
a polymerizable portion that includes at least one polymerizable promotor and at least one polymerizable resin;
at least one photoinitiator in an amount so that a portion of the dental composition at least partially polymerizes and adheres to a dental substrate when the dental composition is exposed to radiant energy and at least part of an exposed surface of the polymerizable portion remains at least partially unpolymerized and deformable when the dental composition is exposed to radiant energy to initiate polymerization of the polymerizable portion during use; and
at least one chemical initiator that does not cause the polymerizable material to polymerize when initially mixed therewith but that causes further polymerization of the polymerizable portion when the dental composition is contacted with an amalgam restorative during use.

64. A dental composition as defined in claim 63, wherein the polymerizable material comprises at least one polymerizable promotor that comprises, or is an oligomer of, at least one monomer having the formula:

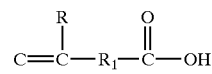

wherein R is a hydrogen radical, a methyl group, a saturated aliphatic radical, an unsaturated aliphatic radical, a halogen radical or a CN radical; and wherein $R_1$ is a chemical bond, at least one an oxygen radical, a saturated aliphatic radical, a saturated aliphatic radical interrupted by at least one oxygen or other polar radical, an unsaturated aliphatic radical, an unsaturated aliphatic radical interrupted by at least one oxygen or other polar radical, a homocyclic radical, a heterocyclic radical, a polymerizable moiety, or an aryl radical having four to six carbon atoms and a valency of n+1, with n being an integer of at least 6.

65. A dental composition as defined in claim 63, wherein the polymerizable material comprises at least one polymerizable resin that comprises at least one of a hydrophilic resin having at least one hydroxy group or a hydrophobic resin.

66. A dental composition as defined in claim 65, wherein the polymerizable resin comprises at least one of the following groups:

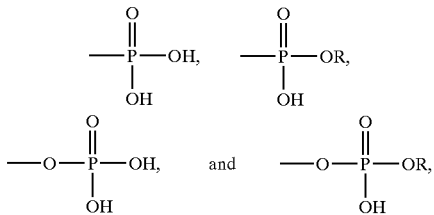

wherein R is an alkyl.

67. A dental composition for bonding an amalgam restorative to a dental substrate, comprising:
  at least two polymerizable materials, one of which is Bis-GMA in a concentration of up to about 4% by weight of the dental composition;
  at least one photoinitiator in an amount that is less than what is stoichiometrically required to cause complete polymerization of the polymerizable material if irradiated with radiant energy in the absence of oxygen; and
  at least one chemical initiator that is initially stable when mixed with the photoinitiator and polymerizable material but that decomposes when exposed to one or more metals contained in an amalgam restorative in order to cause further polymerization of the polymerizable material when the dental composition is contacted with an amalgam restorative during use.

68. A dental composition as defined in claim 67, wherein the Bis-GMA has a concentration of less than about 3% by weight of the dental composition.

69. A dental composition as defined in claim 67, wherein the Bis-GMA has a concentration of less than about 2% by weight of the dental composition.

70. A dental composition for bonding an amalgam restorative to a dental substrate, comprising:
  at least one polymerizable material;
  at least one photoinitiator in an amount so that at least a portion of the polymerizable material remains at least partially unpolymerized when the dental composition is exposed to radiant energy to initiate polymerization of the polymerizable material during use;
  at least one chemical initiator that causes further polymerization of the polymerizable material when the dental composition is contacted with an amalgam restorative during use; and
  barium oxide glass.

71. A dental composition for bonding an amalgam restorative to a dental substrate, comprising:
  at least one polymerizable material;
  at least one photoinitiator in an amount so that at least a portion of the polymerizable material remains at least partially unpolymerized when the dental composition is exposed to radiant energy to initiate polymerization of the polymerizable material during use;
  at least one chemical initiator that causes further polymerization of the polymerizable material when the dental composition is contacted with an amalgam restorative during use; and
  calcium fluorosilicate.

* * * * *

UNITED STATES PATENT AND TRADEMARK OFFICE
CERTIFICATE OF CORRECTION

PATENT NO. : 6,756,417 B2
DATED : June 29, 2004
INVENTOR(S) : Peter M. Allred et al.

It is certified that error appears in the above-identified patent and that said Letters Patent is hereby corrected as shown below:

Column 3,
Line 67, after "so as" insert -- to --

Column 12,
Line 48, after "polymerizable" change "materials" to -- material --

Column 14,
Line 1, after "level of" change "partially" -- partial --

Column 16,
Line 38, before "bonding" change "denting" to -- dental --
Line 55, after "they may" change "reactive" to -- reactivate --

Column 37,
Line 57, after "at least one" remove "an"

Signed and Sealed this

Tenth Day of May, 2005

JON W. DUDAS
*Director of the United States Patent and Trademark Office*